US012576192B2

(12) United States Patent
D'Amore et al.

(10) Patent No.: US 12,576,192 B2
(45) Date of Patent: Mar. 17, 2026

(54) MULTI-LAYERED GRAFT FOR TISSUE ENGINEERING APPLICATIONS

(71) Applicants: University of Pittsburgh—Of the Commonwealth System of Higher Education, Pittsburgh, PA (US); Ri.MED Foundation, Palermo (IT)

(72) Inventors: Antonio D'Amore, Pittsburgh, PA (US); Matteo Solazzo, Dublin (IE); William R. Wagner, Gibsonia, PA (US)

(73) Assignees: University of Pittsburgh—Of the Commonwealth System of Higher Education, Pittsburgh, PA (US); Ri.MED Foundation, Palermo (IT)

( * ) Notice: Subject to any disclaimer, the term of this patent is extended or adjusted under 35 U.S.C. 154(b) by 29 days.

(21) Appl. No.: 18/244,351

(22) Filed: Sep. 11, 2023

(65) Prior Publication Data

US 2024/0216587 A1       Jul. 4, 2024

Related U.S. Application Data

(63) Continuation of application No. 16/634,539, filed as application No. PCT/US2018/043889 on Jul. 26, 2018, now abandoned.

(60) Provisional application No. 62/537,143, filed on Jul. 26, 2017.

(51) Int. Cl.
| | |
|---|---|
| *A61L 31/04* | (2006.01) |
| *A61L 31/12* | (2006.01) |
| *A61L 31/14* | (2006.01) |
| *A61L 31/16* | (2006.01) |
| *A61L 33/00* | (2006.01) |

(52) U.S. Cl.
CPC ........... *A61L 31/047* (2013.01); *A61L 31/125* (2013.01); *A61L 31/146* (2013.01); *A61L 31/148* (2013.01); *A61L 31/16* (2013.01); *A61L 33/0005* (2013.01); *A61L 2430/22* (2013.01); *A61L 2430/40* (2013.01)

(58) Field of Classification Search
CPC .. A61L 31/146; A61L 31/148; A61L 2430/22; C12N 2533/90
See application file for complete search history.

(56) References Cited

U.S. PATENT DOCUMENTS

| | | |
|---|---|---|
| 8,361,503 B2 | 1/2013 | Badylak et al. |
| 8,642,336 B2 | 2/2014 | Vacanti et al. |
| 8,691,276 B2 | 4/2014 | Badylak et al. |
| 9,115,336 B2 | 8/2015 | Hiles et al. |
| 9,421,307 B2 | 8/2016 | Amoroso et al. |
| 2007/0237973 A1 | 10/2007 | Purdy et al. |
| 2013/0253663 A1* | 9/2013 | Amoroso ............... A61L 27/48 623/23.75 |
| 2014/0309726 A1* | 10/2014 | Wang ...................... A61L 27/54 623/1.46 |
| 2015/0010510 A1 | 1/2015 | Badylak et al. |
| 2015/0081010 A1 | 3/2015 | Matheny |
| 2016/0067375 A1 | 3/2016 | Holmes et al. |
| 2017/0007388 A1 | 1/2017 | Neal et al. |
| 2017/0173217 A1 | 6/2017 | Badylak et al. |
| 2017/0281826 A1 | 10/2017 | Monleon Pradas et al. |
| 2019/0015552 A1 | 1/2019 | Badylak et al. |

FOREIGN PATENT DOCUMENTS

| | | |
|---|---|---|
| WO | 2011150055 A2 | 12/2011 |
| WO | 2014144488 A1 | 9/2014 |
| WO | 2017123883 A1 | 7/2017 |

OTHER PUBLICATIONS

Mi, Industrial & Engineering Chemistry Research, 55, 2016 (Year: 2016).*
Dall'Olmo, Biomed Research International, 2014 (Year: 2014).*
D'Amore et al., "Bi-layered polyurethane—Extracellular matrix cardiac patch improves ischemic ventricular wall remodeling in a rat model", Biomaterials, 2016, pp. 1-14, vol. 107.
Goda et al., "Critical update on 2-methacryloyloxyethyl phosphorylcholine (MPC) polymer science", J. Appl. Polym. Sci, 2015, pp. 1-10, vol. 132.
Guan et al., "Synthesis, characterization, and cytocompatibility of elastomeric, biodegradable poly(ester-urethane) ureas based on poly(caprolactone) and putrescine", Journal of Biomedical Materials Research, 2002, pp. 493-503, vol. 61:3.
Krawiec et al., "In Vivo Functional Evaluation of Tissue-Engineered Vascular Grafts Fabricated Using Human Adipose-Derived Stem Cells from High Cardiovascular Risk Populations", Tissue Engineering: Part A, 2016, pp. 765-775, vol. 22:9, 10.
L'Heureux et al., "Human tissue-engineered blood vessels for adult arterial revascularization", Nature Medicine, 2006, pp. 361-365, vol. 12:3.
Liu et al., "A bio-inspired high strength three-layer nanofiber vascular graft with structure guided cell growth", J. Mater. Chem. B., 2017, pp. 3758-3764, vol. 5.
Malkin et al., "Development of Zwitterionic Sulfobetaine Block Copolymer Conjugation Strategies for Reduced Platelet Deposition in Respiratory Assist Devices", J Biomed Mater Res B Appl Biomater, 2018, pp. 2681-2692, vol. 106:7.
Marcolin et al., "Electrospun silk fibroin-gelatin composite tubular matrices as scaffolds for small diameter blood vessel regeneration", J Mater Sci: Mater Med, 2017, 12 pages, vol. 28:80.
Mi et al., "Approaches to Fabricating Multiple-Layered Vascular Scaffolds Using Hybrid Electrospinning and Thermally Induced Phase Separation Methods", Ind. Eng. Chem. Res., 2016, pp. 882-892, vol. 55.

(Continued)

*Primary Examiner* — Robert A Wax
*Assistant Examiner* — William Craigo
(74) *Attorney, Agent, or Firm* — The Webb Law Firm

(57) ABSTRACT

A multi-layer device is provided that is useful in tissue regeneration, for example, for vascular regeneration, e.g., for use in treatment of a coronary vascular disease, such as for treatment of myocardial infarction. A method of making the device also is provided.

19 Claims, 13 Drawing Sheets

(56)    References Cited

OTHER PUBLICATIONS

Soletti et al., "A seeding device for tissue engineered tubular structures", Biomaterials, 2006, pp. 4863-4870, vol. 27.

Takanari et al., "Abdominal wall reconstruction by a regionally distinct biocomposite of extracellular matrix digest and a biodegradable elastomer", J Tissue Eng Regen Med, 2016, pp. 748-761, vol. 10.

Ye et al., "Hollow Fiber Membrane Modification with Functional Zwitterionic Macromolecules for Improved Thromboresistance in Artificial Lungs", Langmuir, 2015, pp. 2463-2471, vol. 31:8.

Ye et al., "Nonthrombogenic, Biodegradable Elastomeric Polyurethanes with Variable Sulfobetaine Content", ACS Appl. Mater. Interfaces, 2014, pp. 22796-22806, vol. 6.

Zhang et al., "Fabrication of three-dimensional poly(E-caprolactone) scaffolds with hierarchical pore structures for tissue engineering", Materials Science and Engineering C, 2013, pp. 2094-2103, vol. 33.

Zhang et al., "In vivo biocompatibility and hemocompatibility of a polytetrafluoroethylene small diameter vascular graft modified with sulfonated silk fibroin", The American Journal of Surgery, 2017, pp. 87-93, vol. 213.

* cited by examiner

NATIVE

SCAFFOLD

CROSS SECTION

LONGITUDINAL SECTION

NATIVE          ES 100 µm          ES 200 µm          ES 300 µm

*Fig. 9E*

MULTI-LAYERED GRAFT FOR TISSUE ENGINEERING APPLICATIONS

CROSS REFERENCE TO RELATED APPLICATIONS

This application is a continuation of U.S. patent application Ser. No. 16/634,539, filed Jan. 27, 2020, which is the United States National Phase of International Application No. PCT/US2018/043889, filed Jul. 26, 2018, and which claims the benefit of U.S. Provisional Patent Application No. 62/537,143 filed Jul. 26, 2017, each of which are incorporated herein by reference in their entirety.

Coronary Heart Disease (CHD) affects 2-6% of the general population currently representing the most common cause of death in the developed countries with a total of 660 k/year coronary attacks and 400 k deaths/year in the USA only. The speed in restoring physiological perfusion conditions compromised by vessels stenosis is a major factor regardless of the different therapeutic intervention approaches currently available. Early stage critical lesions are typically treated with angioplasty (with/without stent support). Whereas, golden standard to treat more severe conditions involves coronary artery bypass graft via autologous vessels such as the saphenous vein, the internal thoracic artery, the radial artery or the gastroepiploic artery.

Yet, due to limited tissue availability, relatively inadequate performance and substantial donor-site morbidity the native vessel transplants remain sub-optimal therapies. These limitations have stressed the importance to continue efforts in searching for alternative vascular grafts with improved incremental outcomes. While being characterized by an extended half-life, non-degradable materials such as PET (Dacron®) and ePTFE (Teflon®) require daily anticoagulation therapy and generally induce mechanical mismatch at the prosthesis-tissue interface. Biological tissue (e.g., dECM, UBM, SIS) based graft has introduced a number of advantages when compared to PET and ePTFE conduits. However, control over device structure and function was partial due to the substantial dependence on the tissue source and decellularization protocol. Most importantly, thrombogenicity and intimal hyperplasia still remain a relatively frequent failure mechanism.

Tissue engineered vascular graft (TEVG), based on the notion of endogenous tissue growth, represents a promising solution. The vast majority of the in vivo studies available within the TEVG literature involve non-degradable/degradable devices prepared mainly via electrospinning, TIPS or particulate leaching. While this approach has represented a substantial improvement in terms of capacity to tune graft morphology, bioactivity of the processed synthetic materials is limited when compared to biologic material based grafts.

N. L'Heureux et al. (Human Tissue Engineered Blood Vessel For Adult Arterial Revascularization, Nature Medicine, 2006 March; 12(3):361-5) proposed a three-layered structure fabricated by cell sheets apposition, however the scaffold required high cost and a ~28 weeks processing time. TEVG presented by Zhang et al. (Fabrication of three-dimensional poly(ε-caprolactone) scaffolds with hierarchical pore structure for tissue engineering, *Materials Science and Engineering: C* 33(4) (2013) 2094-2103) showed a three-layered structure, but suffered the major limitation of reduced host cell infiltration due to its nondegradable and non-porous nature. Similarly, Liu et al. (A bio-inspired high strength three-layer nanofiber vascular graft with structure guided cell growth, *Journal of Materials Chemistry B* 5(20) (2017) 3758-3764) introduced a PLA/PCL three-layered design mimicking native structure. Yet, the small pore sizes and the lack of a bioactive component make this prototype not suitable for the acellular host-cell recruitment paradigm. Zhang et al. (In vivo biocompatibility and hemocompatibility of a polytetrafluoroethylene small diameter vascular graft modified with sulfonated silk fibroin, *Am. J. Surg.* 213(1) (2017) 87-93) developed a three-layered design combining electrospinning and braiding of silk fibroin and poly(L-lactide-co-ε-caprolactone). Unfortunately, graft mechanical compliance was underphysiological with the artificial vessel being generally stiffer than the native one.

There is a need for a processing technique and associated devices for use in preparation of vascular grafts that provide industrial scalability. There is also a need for graft structures that duplicate native tissue functional heterogeneity.

SUMMARY OF THE INVENTION

Provided herein are methods and systems that overcome the aforementioned limitations by combining the merits and benefits of both synthetic (e.g., improved control on structure and function) and biologic tissue derived scaffolds (e.g., bioactivity). To mimic the structure and function of native blood vessels, the biohybrid, three-layered graft design presented herein is based on native tissue functional heterogeneity (e.g., presence of anatomically distinct components specialized to fulfill a specific function).

In one aspect, a method of making a synthetic tubular graft device is provided. The method comprises depositing an ECM gel layer over a first tubular, porous, biodegradable polymer matrix; and depositing a second tubular, porous, biodegradable polymer matrix over the ECM gel to produce a tubular structure.

In another aspect, a multi-layer synthetic graft device is provided. The device comprises a first porous, biodegradable polymer matrix; an ECM gel layer over the first porous, biodegradable polymer matrix; and a second porous, biodegradable polymer matrix over the ECM gel.

In yet another aspect, a method of producing, repairing or replacing a tissue in a patient is provided. The method comprises implanting in the patient a multi-layer synthetic graft device in the patient. The device comprises a first porous, biodegradable polymer matrix; an ECM gel layer over the first porous, biodegradable polymer matrix; and a second porous, biodegradable polymer matrix over the ECM gel.

In another aspect, a kit is provided. The kit comprises a multi-layer synthetic graft device in suitable packaging, such as a foil and/or plastic pouch or container, such as a Mylar package. The device comprises a first porous, biodegradable polymer matrix; an ECM gel layer over the first porous, biodegradable polymer matrix; and a second porous, biodegradable polymer matrix over the ECM gel.

BRIEF DESCRIPTION OF THE DRAWINGS

FIG. 8A) Right coronary arteries (RCA, n=3). FIG. 8B) Left Circumflex coronary arteries (LCx, n=3). FIG. 8C) Left Anterior Descending coronary arteries (LAD, n=2). FIG. 8D) Cumulative average for the coronary arteries (n=8).

FIGS. 9A-9E: Global mechanical compliance. Pressure-volume test results for engineered graft with 3 different ES layer thickness values (data presented as mean±st. deviation) including: FIG. 9A) 100 μm (n=4), FIG. 9B) 200 μm (n=4), FIG. 9C) 300 μm (n=3). FIG. 9D) Native vs. engineered graft comparison. FIG. 9E) global mechanical compliance comparison, showing physiologically relevant compliance values.

FIG. 10A) ES=100 μm (n=3), FIG. 10B) 200 μm (n=3), FIG. 10C) 300 μm (n=3). FIG. 10D) native vs. engineered vessel comparison. Results were presented as mean±st. deviation and showed 1) comparable values of retention force, 2) capacity to tune the retention force by increasing ES thickness.

DETAILED DESCRIPTION

Figures 1A, 1B:
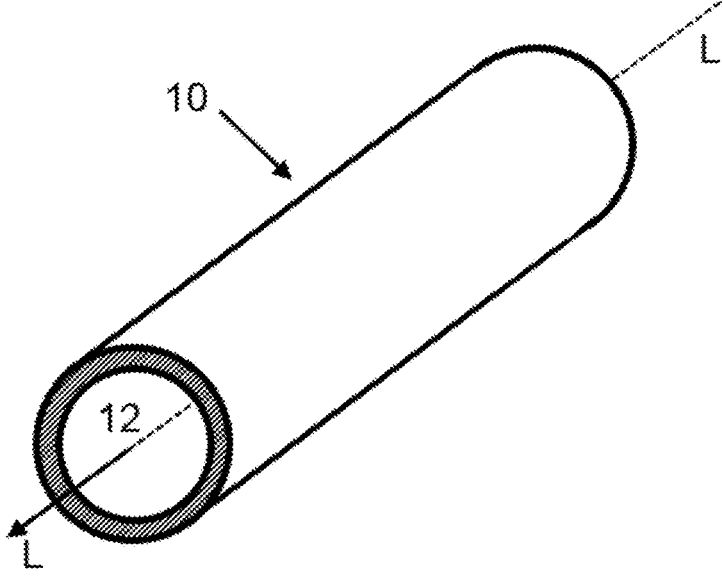
FIG. 1A is a schematic diagram of a graft device according to one aspect of the present invention.
FIG. 1B is a cross-section of the device shown in FIG. 1A on a plane perpendicular to the longitudinal axis L.

Other than in the operating examples, or where otherwise indicated, the use of numerical values in the various ranges specified in this application are stated as approximations as though the minimum and maximum values within the stated ranges are both preceded by the word "about". In this manner, slight variations above and below the stated ranges can be used to achieve substantially the same results as values within the ranges. Also, unless indicated otherwise, the disclosure of ranges is intended as a continuous range including every value between the minimum and maximum values. As used herein "a" and "an" refer to one or more.

As used herein, the term "comprising" is open-ended and may be synonymous with "including", "containing", or "characterized by". The term "consisting essentially of" limits the scope of a claim to the specified materials or steps and those that do not materially affect the basic and novel characteristic(s) of the claimed invention. The term "consisting of" excludes any element, step, or ingredient not specified in the claim. As used herein, embodiments "comprising" one or more stated elements or steps also include, but are not limited to embodiments "consisting essentially of" and "consisting of" these stated elements or steps. For definitions provided herein, those definitions refer to word forms, cognates and grammatical variants of those words or phrases.

As used herein, the term "patient" or "subject" refers to members of the animal kingdom including but not limited to human beings and "mammal" refers to all mammals, including, but not limited to human beings.

As used herein, "treatment" or "treating" of a wound or defect means administration to a patient by any suitable dosage regimen, procedure and/or administration route of a composition, device or structure with the object of achieving a desirable clinical/medical end-point including attracting progenitor cells, healing a wound, correcting a defect, etc.

As used herein, the terms "cell" and "cells" refer to any types of cells from any animal, such as, without limitation, rat, mice, monkey, and human. For example and without limitation, cells can be progenitor cells, such as stem cells, or differentiated cells, such as endothelial cells and smooth muscle cells. In certain aspects, cells for medical procedures can be obtained from the patient for autologous procedures, or from other donors for allogeneic procedures.

As used herein, the term "polymer composition" is a composition comprising one or more polymers. As a class, "polymers" includes, for example and without limitation, homopolymers, heteropolymers, copolymers, block co-polymers and can be both natural and synthetic. Homopolymers contain one type of building block, or monomer, whereas copolymers contain more than one type of monomer.

A polymer "comprises" or is "derived from" a stated monomer if that monomer is incorporated into the polymer. Thus, the incorporated monomer that the polymer comprises is not the same as the monomer prior to incorporation into the polymer, in that at the very least, during incorporation of the monomer, certain groups, e.g., terminal groups, that are modified during polymerization are changed, removed, and/or relocated, and certain bonds may be added, removed, and/or modified. An incorporated monomer is referred to as a "residue" of that monomer. A polymer is said to comprise a specific type of linkage if that linkage is present in the polymer, thus, a polyester comprises a plurality of ester linkages, a polyurethane comprises a plurality of urethane (carbamate) linkages, and a poly(ester urethane) urea comprises ester, urethane, and urea linkages. Unless otherwise specified, molecular weight for polymer compositions refers to weight average molecular weight (Mw). A "moiety" is a portion of a molecule, compound or composition, and includes a residue or group of residues within a larger polymer.

A bioerodible polymer is a polymer that degrades in vivo over a time period, which can be tailored to erode over a time period ranging from days to months, and up to two years, for example, a polymeric structure, when placed in vivo, will fully degrade within a time period of up to two years. By "bioerodible," it is meant that a polymer, once implanted and placed in contact with bodily fluids and/or tissues, will degrade either partially or completely through chemical, biochemical and/or enzymatic processes. Non-limiting examples of such chemical reactions include acid/base reactions, hydrolysis reactions, and enzymatic cleavage. In certain non-limiting embodiments, the biodegradable polymers may comprise homopolymers, copolymers, and/or polymeric blends comprising, without limitation, one or more of the following monomers: glycolide, lactide, caprolactone, dioxanone, and trimethylene carbonate. In other non-limiting embodiments, the polymer(s) comprise labile chemical moieties, non-limiting examples of which include esters, anhydrides, or polyanhydrides, which can be useful in, for example and without limitation, controlling the degradation rate of the scaffold or particles and/or the release rate of therapeutic agents, such as the conditioned medium, from the scaffold or particles.

By "biocompatible," it is meant that a polymer composition and its normal degradation in vivo products are cytocompatible and are substantially non-toxic and non-carcinogenic in a patient within useful, practical and/or acceptable tolerances. By "cytocompatible," it is meant that the polymer can sustain a population of cells and/or the polymer composition, device, and degradation products thereof are not cytotoxic and/or carcinogenic within useful, practical, and/or acceptable tolerances. For example, the polymer when placed in a human epithelial cell culture does not adversely affect the viability, growth, adhesion, and number of cells. In one non-limiting embodiment, the compositions and/or devices are "biocompatible" to the extent they are acceptable for use in a human or veterinary patient according to applicable regulatory standards in a given jurisdiction. In another example, the biocompatible polymer, when implanted in a patient, does not cause a substantial adverse reaction or substantial harm to cells and tissues in the body, for instance, the polymer composition or device does not cause unacceptable inflammation, necrosis, or an infection resulting in harm to tissues from the implanted scaffold. A "patient" is a human or non-human animal.

Non-limiting examples of a bioerodible polymer useful for tissue or vascular growth scaffolds or the described particles described herein include: a polyester, a polyester-containing copolymer, a polyanhydride, a polyanhydride-containing copolymer, a polyorthoester, and a polyorthoester-containing copolymer. In one aspect, the polyester or polyester-containing copolymer is a poly(lactic-co-glycolic) acid (PLGA) copolymer. In another embodiment, the bioerodible polymer is selected from the group consisting of poly(lactic acid) (PLA); poly(trimethylene carbonate) (PTMC); poly(caprolactone) (PCL); poly(glycolic acid) (PGA); poly(glycolide-co-trimethylenecarbonate) (PGTMC); poly(L-lactide-co-glycolide) (PLGA); polyethylene-glycol (PEG-) containing block copolymers; and polyphosphazenes. Additional bioerodible, biocompatible polymers include: a poly(ester urethane) urea (PEUU); poly(ether ester urethane)urea (PEEUU); poly(ester carbonate)urethane urea (PECUU); poly(carbonate)urethane urea (PCUU); a polyurethane; a polyester; a polymer comprising monomers derived from alpha-hydroxy acids such as: polylactide, poly(lactide-co-glycolide), poly(L-lactide-co-caprolactone), polyglycolic acid, poly(dl-lactide-co-glycolide), and/or poly(l-lactide-co-dl-lactide); a polymer comprising monomers derived from esters including polyhydroxybutyrate, polyhydroxyvalerate, polydioxanone, and/or polyglactin; a polymer comprising monomers derived from lactones including polycaprolactone; or a polymer comprising monomers derived from carbonates including polycarbonate, polyglyconate, poly(glycolide-co-trimethylene carbonate), or poly(glycolide-co-trimethylene carbonate-co-dioxanone).

Non-erodable polymers either do not erode substantially in vivo or erode over a time period of greater than two years. Compositions such as, for example and without limitation, PTFE, poly(ethylene-co-vinyl acetate), poly(n-butylmethacrylate), poly(styrene-b-isobutylene-b-styrene) and polyethylene terephthalate are considered to be non-erodable polymers. Other suitable non-erodable polymer compositions are broadly known in the art, for example, in stent coating and transdermal reservoir technologies. The growth scaffolds described herein may comprise a non-erodible polymer composition.

In some examples, one or more layers of the device may be formed from a biodegradable and biocompatible scaffold material, such as a synthetic polymeric composition comprising poly(ester-urethane)urea (PEUU). PEUU can be synthesized using putrescine as a chain extender and a two-step solvent synthesis method. For example, a poly (ester urethane) urea elastomer (PEUU) may be made from polycaprolactonediol (MW 2,000) and 1,4-diisocyanatobutane, with a diamine, such as putrescine as the chain extender. A suitable PEUU polymer may be made by a two-step polymerization process whereby polycaprolactone diol (Mw 2,000), 1,4-diisocyanatobutane, and putrescine are combined in a 1:2:1 molar ratio, though virtually any molar feed ratio may suffice so long as the molar ratio of each monomer component is >0. In one embodiment, the molar feed ratio of polycaprolactone diol plus putrescine is equal to that of diisocyanatobutane. In the first polymerization step, a 15 wt % solution of 1,4-diisocyanatobutane in DMSO is stirred continuously with a 25 wt % solution of diol in DMSO. In the second step, stannous octoate is added and the mixture is allowed to react at 75° C. for 3 hours, with the addition of triethylamine to aid dissolution. A poly(ether ester urethane) urea elastomer (PEEUU) may be made by reacting polycaprolactone-b-polyethylene glycol-b-polycaprolactone triblock copolymers with 1,4-diisocyanatobutane and putrescine. In a preferred embodiment, PEEUU is obtained by a two-step reaction using a 2:1:1 reactant stoichiometry of 1,4-diisocyanatobutane:triblock copolymer:putrescine. In the first polymerization step, a 15 wt % solution of 1,4-diisocyanatobutane in DMSO is stirred continuously with a 25 wt % solution of triblock compolymer diol in DMSO. In the second step, stannous octoate is added and the mixture is allowed to react at 75° C. for 3 hours. The reaction mixture is then cooled to room temperature and allowed to continue for 18 h. The PEEUU polymer solution is then precipitated with distilled water and the wet polymer is immersed in isopropanol for 3 days to remove unreacted monomer and dried under vacuum.

In another aspects, one or more layers of the device is formed from a poly(ester carbonate urethane)urea (PECUU) or poly(carbonate)urethane urea (PCUU) material. PECUU and PCUU are described, for example, in Hong et al. (Tailoring the degradation kinetics of poly(ester carbonate urethane)urea thermoplastic elastomers for tissue engineering scaffolds Biomaterials, doi:10.1016/j.biomaterials.2010.02.005). PECUU is synthesized, for example, using a blended soft segment of polycaprolactone (PCL) and poly(1,6-hexamethylene carbonate) (PHC) and a hard segment of 1,4-diisocyanatobutane (BDI) with chain extension by putrescine. Different molar ratios of PCL and PHC can be used to achieve different physical characteristics. Putrescine is used as a chain extender by a two-step solvent synthesis method. In one example, the (PCL+PHC):BDI:putrescine molar ratio is defined as 1:2:1. Variable molar ratios of PCL and PHC (e.g., PCL/PHC ratios of 100/0 (yielding a PEUU), 75/25, 50/50, 25/75 and 0/100 (yielding a PCUU)) are completely dissolved in DMSO in a 3-neck flask with argon protection and then BDI is added to the solution, following 4 drops of Sn(Oct)2. The flask is placed in an oil bath at 70° C. After 3 h, the prepolymer solution is cooled at room temperature and then a putrescine/DMSO solution is added dropwise into the agitated solution. The final polymer solution concentration is controlled to be approximately 4% (w/v). Then the flask is than placed in an oil bath and kept at 70° C. overnight. The polymer is precipitated in an excess volume of cool deionized water and then dried in a vacuum at 60° C. for 3 days. The polyurethane ureas synthesized from the different PCL/PHC molar ratios defined above are referred to as PEUU, PECUU 75/25, PECUU 50/50, PECUU 25/75 and PCUU, respectively. In practice, the yields of all final products using this method is approximately 95%.

In aspects, a polymer composition may be anti-thrombogenic, meaning the polymer includes a moiety that resists formation of a thrombus. Anti-thrombogenic polymer compositions are known in the medical arts. In one aspect, a polymer composition, such as a polyanhydride, a polyester, a polyurethane, PCUU, PECUU, PEUU, PEEUU, and polyacrylates are modified with a zwitterion moiety, either incorporated into the backbone of the polymer or pendant therefrom. In one example, an antithrombogenic polymer comprises a pendant phosphorylcholine, such as in a polymer composition comprising 2-methacryloyloxyethyl phosphorylcholine (MPC) (see, e.g., Goda, T., et al., Critical update on 2-methacryloyloxyethyl phosphorylcholine (MPC) polymer science. *J. Appl. Polym. Sci.* 2015, DOI: 10.1002/APP.41766). In another example, a sulfobetaine moiety is incorporated into a polymer composition, as in Ye, S. et al. (Nonthrombogenic, Biodegradable Elastomeric Polyurethanes with Variable Sulfobetaine Content. *ACS Appl. Mater. Interfaces,* 2014, 6 (24), pp 22796-22806). Additional sulfobetaine- or phosphorocholine-containing polymer compositions are described in Ye, S., et al. (Hollow Fiber Membrane Modification with Functional Zwitterionic Macromolecules for Improved Thromboresistance in Artificial Lungs *Langmuir* 2015 31 (8), 2463-2471) and in Malkin, A. D., et al. (Development of Zwitterionic Sulfobetaine Block Copolymer Conjugation Strategies for Reduced Platelet Deposition in Respiratory Assist Devices *J Biomed Mater Res B Appl Biomater.* 2018 Feb. 9. doi: 10.1002/jbm.b.34085).

Methods of preparation of the polymeric compositions described herein are broadly-known. For example, diamines and diols are useful building blocks for preparing the described polymer compositions. Diamines as described above have the structure $H_2N$—R—$NH_2$ where "R" is an aliphatic or aromatic hydrocarbon or a hydrocarbon comprising aromatic and aliphatic regions. The hydrocarbon may be linear or branched. Examples of useful diamines are putrescine (R=butylene) and cadaverine (R=pentylene). Useful diols include polycaprolactone (e.g., Mw 1000-5000), multi-block copolymers, such as polycaprolactone-PEG copolymers, including polycaprolactone-b-polyethylene glycol-b-polycaprolactone triblock copolymers of varying sizes. Other building blocks for useful diols include, without limitation glycolides (e.g., polyglycolic acid (PGA)), lactides, dioxanones, and trimethylene carbonates. Diisocyanates have the general structure OCN—R—NCO, where "R" is an aliphatic or aromatic hydrocarbon or a hydrocarbon comprising aromatic and aliphatic regions. The hydrocarbon may be linear or branched.

As used herein, the terms "extracellular matrix" and "ECM" refer to a natural scaffolding for cell growth. ECM is a complex mixture of structural and non-structural biomolecules, including, but not limited to, collagens, elastins, laminins, glycosaminoglycans, proteoglycans, antimicrobials, chemoattractants, cytokines, and growth factors. In mammals, ECM often comprises about 90% collagen in its various forms. The composition and structure of ECMs vary depending on the source of the tissue. For example, small intestine submucosa (SIS), urinary bladder matrix (UBM), liver stroma ECM, and dermal ECM each differ in their overall structure and composition due to the unique cellular niche needed for each tissue.

As used herein, the term "derive" and any other word forms or cognates thereof, such as, without limitation, "derived" and "derives", refers to a component or components obtained from any stated source by any useful method. For example and without limitation, generically, an ECM-derived gel refers to a gel comprised of components of ECM obtained from any tissue by any number of methods known in the art for isolating ECM. In another example, mammalian tissue-derived ECM refers to ECM comprised of components of a particular mammalian tissue obtained from a mammal by any useful method.

The methods described herein involve preparation of ECM or an ECM gel. The ECM gel is reverse gelling, or can be said to exhibit reverse thermal gelation, in that it forms a gel upon an increase in temperature. As the temperature rises above a certain temperature in a reverse gel, a hydrogel is formed. The general concept of reverse gelation of polymers is broadly known in the chemical arts (see, e.g., U.S. Pat. Nos. 8,361,503 and 8,691,276, U.S. Patent Application Publication Nos. 20150010510 and 20170173217, and International Patent Application No. PCT/US2017/013355, each of which is incorporated herein by reference for its technical disclosure). International Patent Application No. PCT/US2017/013355 discloses and describes ECM gel prepared from vascular sources. The ECM compositions described herein are prepared, for example, from decellularized or devitalized, intact tissue as described below. An ECM gel is prepared by digestion of the ECM material with an acid protease, neutralization of the material to form a pre-gel, and then raising the temperature of the pre-gel above a gelation temperature, for example, the lower critical solution temperature (LCST) of the pre-gel, to cause the pre-gel to gel. As used herein, the term "gel" includes hydrogels. The transition temperature for acid-protease-digested from solution to gel is typically within the range of from 10° C. to 40° C. and any increments or ranges therebetween, for example, from 20° C. to 35° C. For example, the pre-gel can be warmed to 37° C. to form a hydrogel.

Tissue for preparation of ECM, ECM-derived pre-gel solutions, and gels as described herein may be harvested in any useful manner. According to various aspects, the ECM materials described herein are prepared from vascular tissue, such as vascular adventitia (tunica adventitia), vascular media (tunica media), and/or intima (tunica intima) tissue, such as arterial or venous tissue, such as aortic tissue. For example and without limitation, in one aspect, the ECM material is prepared from harvested porcine aorta, and in another, from human aorta. If a portion of the blood vessel is used, such as one or two of the vascular adventitia, media, or tunica, the portion is dissected from the harvested tissue, and is optionally frozen. Arterial or venous, e.g., aorta tissue, is obtained by any suitable method, for example, by manually isolating from the surrounding tissue. In one aspect, the ECM gel is prepared from vascular tunica media. In another aspect, the ECM gel is prepared from vasculature including intima, media, and/or adventitia layers, e.g., an intact blood vessel including intima, media, and adventitia layers.

Decellularized or devitalized tissue can be dried, either lyophilized (freeze-dried) or air dried. The ECM composition is optionally comminuted at some point, for example, prior to acid protease digestion in preparation of an ECM gel, for example, prior to or after drying. The comminuted ECM can also be further processed into a powdered form by methods, for example and without limitation, such as grinding or milling in a frozen or freeze-dried state. As used herein, the term "comminute" and any other word forms or cognates thereof, such as, without limitation, "comminution" and "comminuting", refers to the process of reducing larger particles, e.g., of dried ECM, into smaller particles, including, without limitation, by tearing, grinding, blending, shredding, slicing, milling, cutting, shredding, shearing, and pulverizing. ECM can be comminuted while in any form, including, but not limited to, hydrated forms, frozen, air-dried, lyophilized, powdered, sheet-form.

In order to prepare solubilized ECM tissue, ECM, for example, comminuted ECM, is digested with an acid protease in an acidic solution to form a digest solution. As used herein, the term "acid protease" refers to an enzyme that cleaves peptide bonds, wherein the enzyme has increased activity of cleaving peptide bonds in an acidic pH. A non-limiting example of a suitable acid protease is pepsin.

As an example, the digest solution of ECM is kept at a constant stir for a certain amount of time at room temperature. In one aspect, the pH is maintained at less than pH 4.0 or at pH 2.0±0.3 during acid protease digestion of the decellularized aortic adventitial tissue as described herein. The ECM digest can be used immediately or can be stored at −20° C. or frozen at, for example and without limitation, −20° C. or −80° C. In certain aspects, the ECM digest is snap frozen in liquid nitrogen. To form a "pre-gel solution", the pH of the digest solution is raised to a pH between 6.8 and 7.8. The pH can be raised by adding one or more of a base or a buffer, such as an isotonic buffered solution, for example and without limitation, NaOH or PBS at pH 7.4. The method optionally does not include a dialysis step prior to gelation, yielding a more-complete ECM-like matrix that typically gels at 37° C. more slowly than comparable collagen or dialyzed ECM preparations. The gel therefore retains more of the qualities of native ECM due to retention of many native soluble factors, such as, without limitation, cytokines. These factors contribute to chemoattraction of cells and proper rearrangement of tissue at the site of injury, rather than a fibrotic response that leads to unwanted scarring. In other embodiments, the ECM is dialyzed prior to gelation to remove certain soluble components.

As used herein, the term "isotonic buffered solution" refers to a solution that is buffered to a pH between 6.8 and 7.8, e.g., pH 7.4, and that has a balanced concentration of salts to promote an isotonic environment. As used herein, the term "base" refers to any compound or a solution of a compound with a pH greater than 7. For example and without limitation, the base is an alkaline hydroxide or an aqueous solution of an alkaline hydroxide. In certain aspects, the base is NaOH, or NaOH in PBS. This "pre-gel" solution can, at that point be incubated at a suitably warm temperature, for example and without limitation, at about 37° C. to gel.

In the method of preparing an ECM gel, the ECM may be partially or completely digested with the acid protease, such as pepsin. The degree of digestion of the ECM can be determined by comparison on a gel, or by ascertaining the degree of degradation of hyaluronic acid, for example, by Western blot (anti-hyaluronic acid antibodies are commercially-available from multiple sources) or chromatographic methods, as are broadly known. For example, in a partial digestion, hyaluronic acid is digested less than 50%, 40%, 30%, 25%, 20%, or 10%. As indicated above, the digested ECM is neutralized to a pH of 6.8-7.8, e.g., 7.2-7.6, or 7.4 to produce a pre-gel solution, and the pre-gel solution is gelled by incubation at a temperature at which the material gels, e.g., at a temperature above 20°, 25°, 30°, or 35° C., such as at 37° C.

In one aspect, a multi-layer device is provided, such as a tubular device that is, for example, suitable for replacement of a blood vessel. The device can be characterized as a tissue growth matrix or scaffold in that it is supportive of cell infiltration, cell growth, and/or cell differentiation. In another aspect, the device is formed as a sheet. In yet another aspect, the device is formed in a three-dimensional structure, such as a tube. Layers of the device are porous, in that liquids can pass into, and through the layers. Porosity of the layers can vary, and typically pores (openings) comprise from 10% to 95% of the volume of the layer, such as 10%, 20%, 25%, 30%, 35%, 40%, 50%, 60%, 70%, 75%, 80%, 90%, or 95%. The porosity, shapes, and interconnectivity of the pores can vary from layer-to-layer of the multi-layered device, and depend on the method used to make the respective layer.

Layers can be formed by any useful method, as are broadly-known in the technical field of the invention. For example and without limitation, by phase separation, e.g., by Thermally Induced Phase Separation (TIPS), Non-solvent Induced Phase Separation (NIPS), or Diffusion Induced Phase Separation (DIPS), which are broadly-known processes and may be used independently to prepare one or more layers of the described devices. High-resolution 3D printing technologies can deposit materials with microscale resolution, permitting highly-organized structures, and also may be employed to prepare one or more of the described layers of the device described herein. Porous layers also may be prepared by particulate leaching, that is by dissolution, e.g., in water, of dissolvable particles, such as salt or sugar particles embedded in a polymer structure, for example, a cast or molded polymer structure.

In further detail, TIPS takes advantage of the thermodynamic instability of polymer solutions at certain temperatures. The TIPS phase separation procedure requires the use of a solvent with a low melting point that is easy to sublime. In TIPS, when a polymer is dissolved in a solvent, it becomes thermodynamically unstable at low temperatures and will spontaneously separate into two phases. Once the polymer is dissolved in an appropriate solvent, phase separation is induced through the addition of a small quantity of water. This then results in a polymer-rich and a polymer-poor phase. Following cooling below the solvent melting point and vacuum-drying to sublime the solvent, a porous scaffold is obtained. In NIPS, a polymer solution (that is, a polymer dissolved in a solvent) is immersed in a non-solvent bath (coagulation bath), typically water, where the exchange of solvent and non-solvent takes place. Specifically, the solvent migrates from the polymer solution to the coagulation bath, while the non-solvent follows the reverse path, leading to the formation of the membrane.

Another useful method for producing the tissue structures and/or controlled-release devices is electrodeposition. The polymeric scaffold can be electrospun, e.g., on a mandrel in the case of a tubular tissue scaffold, e.g., a vascular tissue. Electrospinning permits fabrication of scaffolds that resemble the scale and fibrous nature of the native extracellular matrix (ECM). The ECM is composed of fibers, pores, and other surface features at the sub-micron and nanometer size scale. Such features directly impact cellular interactions with synthetic materials such as migration and orientation. Electrospinning also permits fabrication of oriented fibers to result in anisotropic scaffolds. These aligned scaffolds can influence cellular growth, morphology and ECM production.

Generally, the process of electrospinning involves placing a polymer-containing fluid (e.g, a polymer solution, a polymer suspension, or a polymer melt) in a reservoir equipped with a small orifice, such as a needle or pipette tip and a metering pump. One electrode of a high voltage source is also placed in electrical contact with the polymer-containing fluid or orifice, while the other electrode is placed in electrical contact with a target (typically a collector screen or rotating mandrel). During electrospinning, the polymer-containing fluid is charged by the application of high voltage to the solution or orifice (e.g., about 3-15 kV) and then forced through the small orifice by the metering pump that provides steady flow. While the polymer-containing fluid at the orifice normally would have a hemispherical shape due to surface tension, the application of the high voltage causes the otherwise hemispherically shaped polymer-containing fluid at the orifice to elongate to form a conical shape known as a Taylor cone. With sufficiently high voltage applied to the polymer-containing fluid and/or orifice, the repulsive electrostatic force of the charged polymer-containing fluid overcomes the surface tension and a charged jet of fluid is ejected from the tip of the Taylor cone and accelerated towards the target, which typically is biased between −2 to −10 kV. Optionally, a focusing ring with an applied bias (e.g., 1-10 kV) can be used to direct the trajectory of the charged jet of polymer-containing fluid. As the charged jet of fluid travels towards the biased target, it undergoes a complicated whipping and bending motion. If the fluid is a polymer solution or suspension, the solvent typically evaporates during mid-flight, leaving behind a polymer fiber on the biased target. If the fluid is a polymer melt, the molten polymer cools and solidifies in mid-flight and is collected as a polymer fiber on the biased target. As the polymer fibers accumulate on the biased target, a non-woven, porous mesh (matrix) is formed on the biased target.

The properties of the electrospun elastomeric matrices can be tailored by varying the electrospinning conditions. For example, when the biased target is relatively close to the orifice, the resulting electrospun mesh tends to contain unevenly thick fibers, such that some areas of the fiber have a "bead-like" appearance. However, as the biased target is moved further away from the orifice, the fibers of the non-woven mesh tend to be more uniform in thickness. Moreover, the biased target can be moved relative to the orifice. In certain embodiments, the biased target is moved back and forth in a regular, periodic fashion, such that fibers of the non-woven mesh are substantially parallel to each other. When this is the case, the resulting non-woven mesh may be anisotropic, e.g., having a higher resistance to strain in the direction parallel to the fibers, compared to the direction perpendicular to the fibers. In other embodiments, the biased target is moved randomly relative to the orifice, so that the resistance to strain in the plane of the non-woven mesh is isotropic. The target can also be a rotating mandrel. In this case, the properties of the non-woven mesh may be changed by varying the speed of rotation. The properties of the electrospun elastomeric scaffold may also be varied by changing the magnitude of the voltages applied to the electrospinning system.

Electrospinning may be performed using two or more nozzles, wherein each nozzle is a source of a different polymer solution. The nozzles may be biased with different biases or the same bias in order to tailor the physical and chemical properties of the resulting non-woven polymeric mesh. Additionally, many different targets may be used. In addition to a flat, plate-like target, a mandrel may be used as a target.

When the electrospinning is to be performed using a polymer suspension, the concentration of the polymeric component in the suspension can also be varied to modify the physical properties of the elastomeric scaffold. For example, when the polymeric component is present at relatively low concentration, the resulting fibers of the electrospun non-woven mesh have a smaller diameter than when the polymeric component is present at relatively high concentration. Without any intention to be limited by this theory, it is believed that lower concentration solutions have a lower viscosity, leading to faster flow through the orifice to produce thinner fibers. One skilled in the art can adjust polymer concentrations to obtain fibers of desired characteristics. Useful ranges of concentrations for the polymer component include from about 1% wt. to about 15% wt., from about 4% wt. to about 10% wt. and from about 6% wt. to about 8% wt.

Thickness of the matrix can be controlled by either adjusting the viscosity of the polymer composition to be deposited and/or adjusting duration of the electrospinning. Use of more viscous polymer composition may result in thicker fibers, requiring less time to deposit a matrix of a desired thickness. Use of a less viscous polymer composition may result in thinner fibers, requiring increased deposition time to deposit a matrix of a desired thickness. The thickness of the matrix and fibers within the matrix affects the speed of bioerosion of the matrix. These parameters are optimized, depending on the end-use of the matrix, to achieve a desired or optimal physiological effect.

Dry electrospinning refers to electrodeposition of only a polymer composition as described above. In contrast, wet electrospinning employs concurrent electrodeposition, or deposition of liquids during the electrodeposition of the polymer. Suitable liquids include water, saline, PBS, cell culture medium, and any other suitable ingredient, such as one or more therapeutic agents. In practice, while cytocompatible and non-toxic, dry-electrospun layers are often marginally-supportive of cell infiltration, and, as indicated below, can be used as a barrier layer to prevent or retard stenosis of the nascent blood vessel due to intima hyperplasia. In contrast, wet electrospun layers are typically more supportive of cell infiltration.

According to one aspect of the invention, a tubular device is provided comprising three layers. FIG. 1A depicts a tubular device 10 according to one aspect of the invention, having a lumen 12, and a longitudinal axis L. FIG. 1B, depicts a cross section of a tubular device 10, e.g., as shown in FIG. 1A, taken perpendicular to a longitudinal axis of the device 10 and having a lumen 12. FIGS. 1A and 1B are not to scale. FIG. 1B further shows the three-layer structure of device 10, depicting a first layer 20 disposed concentrically about the lumen 12 and defining the lumen 12, a second layer 30 disposed about at least a portion of the circumference of the first layer 20, and a third layer 40 disposed about at least a portion of the circumference of the second layer 30.

As used herein stating that a layer is said to be disposed "over" a referenced layer, or "about a circumference of" a referenced layer, or "about at least a portion of the circumference of" a referenced layer, does not imply the layer is directly adjacent to the referenced layer, and may comprise one or more additional layers therebetween, and further does not imply that the layer completely covers the referenced layer, and may only cover, surround, contact, etc. only a portion of the referenced layer. That said, if a layer is said to be disposed "directly about" or "directly over" a referenced layer, it is meant the two layers contact each other, though an intermediary layer, such as an adhesive layer, or a blended layer that results from directly contacting the two layers during the process of formation of the device may be present between the two stated layers. Also, if a layer is said to "completely cover" a referenced layer, it is meant the second layer covers the entirety of the referenced layer. Stating that a layer is said to be disposed "over" another layer, or "about a circumference of" a referenced layer, or "about at least a portion of the circumference of" a referenced layer includes where the stated layers are directly contacting each other and/or that the layer completely covers the referenced layer. Further, as used herein, recited dimensions are dimensions of the device taken at two or more points, e.g., three points over the longitudinal direction of the device, for example, at the center and at the edges of the segment. Diameters and thicknesses are measured along lines perpendicular to a longitudinal axis of the tubular structures described herein.

In one aspect, in reference to FIG. 1B, the first layer 20 of tubular device 10 does not support cell growth, and, therefore, can be described as a barrier layer. In one aspect the first layer 10 is a dry electrospun bioerodible polymer. In practice, dry-electrospun bioerodible polymers typically do not support substantial migration of and/or proliferation of vascular cells such as vascular smooth muscle cells, thereby discouraging stenosis (e.g., neointimal hyperplasia) of the nascent arterial wall, which often arises from proliferation of vascular smooth muscle cells into the lumen of the artery. The first layer 20 will eventually degrade, but the use of a barrier polymer will prevent stenosis during the formation of the vessel.

Any biocompatible, bioerodible polymer can be used to form the first layer 20, such as a polyester; a polyurethane; a poly(ester urethane) urea (PEUU); poly(ether ester urethane)urea (PEEUU); poly(ester carbonate)urethane urea (PECUU); poly(carbonate)urethane urea (PCUU); a polymer comprising monomers derived from alpha-hydroxy acids such as: polylactide, poly(lactide-co-glycolide), poly (L-lactide-co-caprolactone), polyglycolic acid, poly(dl-lactide-co-glycolide), and/or poly(I-lactide-co-dl-lactide); a polymer comprising monomers derived from esters including polyhydroxybutyrate, polyhydroxyvalerate, polydioxanone, and/or polyglactin; a polymer comprising monomers derived from lactones including polycaprolactone; or a polymer comprising monomers derived from carbonates including polycarbonate, polyglyconate, poly(glycolide-co-trimethylene carbonate), or poly(glycolide-co-trimethylene carbonate-co-dioxanone). Non-erodible polymers, e.g., as described above, can also be utilized, though may not be preferred. The first layer 20 can be electrodeposited, or formed by any other suitable method, such as NIPS or TIPS, though in one aspect, dry electrospinning is used to retard or prevent stenosis.

The second layer 30 comprises an ECM gel, such as a vascular ECM gel. The gel optionally comprises a cell, such as a vascular smooth muscle cell, a vascular endothelial cell, or a progenitor cell of either, such as a mesenchymal stem cell or an adipose-derived stem cell, as are broadly-known and are described elsewhere herein. ECM gels and methods of making such ECM gels are described elsewhere herein.

The third layer 40 is supportive of cell growth, and is a porous, biocompatible, biodegradable polymeric matrix. Any biocompatible, bioerodible polymer can be used to form the first layer 20 and, independently, the third layer 40, such as a polyester; a polyurethane; a poly(ester urethane) urea (PEUU); poly(ether ester urethane)urea (PEEUU); poly (ester carbonate)urethane urea (PECUU); poly(carbonate) urethane urea (PCUU); a polymer comprising monomers derived from alpha-hydroxy acids such as: polylactide, poly(lactide-co-glycolide), poly(L-lactide-co-caprolactone), polyglycolic acid, poly(dl-lactide-co-glycolide), and/or poly (I-lactide-co-dl-lactide); a polymer comprising monomers derived from esters including polyhydroxybutyrate, polyhydroxyvalerate, polydioxanone, and/or polyglactin; a polymer comprising monomers derived from lactones including polycaprolactone; or a polymer comprising monomers derived from carbonates including polycarbonate, polyglyconate, poly(glycolide-co-trimethylene carbonate), or poly (glycolide-co-trimethylene carbonate-co-dioxanone). Non-erodible polymers, e.g., as described above, can also be utilized, though may not be preferred. The first layer 20 and third layer 40, independently, can be electrodeposited, or formed by any other suitable method, such as NIPS or TIPS, though in one aspect, dry electrospinning is used to retard or prevent stenosis. In one aspect, the first layer 20 comprises dry electrospun PEUU and the third layer 40 comprises PEUU prepared by TIPS.

In another aspect, in reference to FIG. 1B, the first layer 20 of tubular device 10 supports cell growth, and the third layer 40 does not, and for example and without limitation, the third layer 40 is a dry electrospun cell growth barrier, and the first layer 20 is supportive of cell growth, and is for example and without limitation, prepared by phase separation or wet electrospinning. A device of this structure is useful for determining the contribution of blood-borne cell infiltration on tissue regeneration in blood vessel grafts as compared to the contribution of infiltrating anastomosis derived cells migrating from adjacent tissue to the graft.

In one aspect, the device has a wall thickness (e.g., in reference to FIG. 1B, a sum of thicknesses of the first layer 20, the second layer 30, and the third layer 40) ranges from 200 μm to 1 mm, from 250 μm to 750 μm, for example 500 μm. In another aspect, the thickness of the combined layers of the first tubular, porous, biodegradable polymer matrix plus the ECM gel (e.g. in reference to FIG. 1B, a sum of thicknesses of the first layer 20 and the second layer 30) ranges from 100 μm to 500 μm, from 150 μm to 350 μm, or from 175 μm to 250 μm. In yet another aspect, the thickness of the second tubular, porous, biodegradable polymer matrix plus the ECM gel (e.g. in reference to FIG. 1B, a sum of thicknesses of the second layer 30 and the third layer 40) ranges from 50 μm to 250 μm, from 75 μm to 125 μm, for example 100 μm. In a further aspect, the lumen of the device has an inner diameter (e.g., in reference to FIG. 1B, a diameter of lumen 12) ranging from 1 mm to 2 mm, from 1.5 mm to 3.5 mm, or 2 mm.

A porous polymer tube is prepared from a suitable biodegradable polymer composition by any method, e.g., by electrospinning or TIPS or molding, and may comprise one or more concentric layers with one layer having a first composition and/or physical structure, a second layer having a second composition and/or a second physical structure, and a third layer having a third composition and/or third physical structure. For example, a first layer may be produced by an electrospinning method, a second layer may be formed/molded around (e.g., concentrically around) the first layer, and a third layer may be deposited by a TIPS method about (e.g., concentrically around) the second layer.

In one aspect, the device is useful for coronary artery repair or bypass and has an internal lumen diameter or dimension approximating that of a coronary artery, e.g., having an inside (lumen) diameter ranging from 1.0 mm to 3.5 mm, and an outer diameter ranging from 2.0 mm to 4.5 mm. In use, the device is anastomosed to existing coronary arteries or to other suitable source blood vessels in order to transfer blood from the source blood vessel into the heart tissue, thereby bypassing a blocked or damaged coronary artery. In another aspect, the device is used to repair or bypass a peripheral blood vessel, and once again having dimensions, such as a lumen diameter and an external diameter approximating native blood vessel dimensions. In that instance, the blood vessel is anastomosed to existing arteries or to other suitable source blood vessels in order to transfer blood from the source blood vessel into the destination tissue, thereby bypassing a blocked or damaged blood vessel. The device can be used for venous or arterial blood vessel repair.

In one aspect, the device is not seeded with cells prior to implantation. Native cells will migrate into the device, either from sources external to the device, e.g., from the anastomosis or other external sources, and/or from blood passing through the device, and populate the device. The materials used to form the device are biodegradable, such that as the device becomes populated with cells, and the cells mature into blood vessel tissue, the scaffolding of the device erodes until only newly-formed blood vessel tissue remains.

In certain aspects, cells are added to the composition. Non-limiting examples of useful cells include: stem cells, progenitor cells and differentiated cells; recombinant cells; muscle cells and precursors thereof; nerve cells and precursors thereof; mesenchymal progenitor or stem cells; bone cells or precursors thereof, such as osteoprogenitor cells, pre-adipocytes, etc. Cells may be from any useful source, including autologous, allogeneic, or from xenogeneic sources, and may be genetically-modified in any useful manner, such as by direct nucleic acid transfer, viral transduction, or gene/genome editing (e.g., CRISPR-Cas, TALEN, meganuclease, or ZFN systems). In one aspect, the cells are vascular endothelial cells, vascular smooth muscle cells, and/or a mesenchymal stem cell, such as an adipose-derived mesenchymal stem cell. Differentiated cells can either be harvested from a patient (e.g., autologous), or differentiated, e.g., from mesenchymal stem cells or adipose-derived stem cells, e.g., autologous adipose-derived stem cells of a patient. Differentiated cells can either be harvested from a patient (e.g., autologous), or differentiated according to broadly-known methods. For example, differentiated blood vessel cells can be harvested directly from venous or arterial tissue of a patient, or mesenchymal stem cells can be encouraged to differentiate into blood vessel cells by culturing on static/dynamic bioreactors with basic or specific cell culture media cell with supplements optimized for specific applications. Matrices as described herein can be populated with live cells by any useful manner. For example, the ECM gel may be mixed with live cells harvested from blood vessels or culture immediately prior to forming an ECM gel layer in the described device. For wet-electrospun layers, cells can be co-deposited with a polymer, for instance by electrospraying, for example, concurrently with the electrodeposition of fiber layers forming the matrix. In another aspect, cells can by vacuum-deposited by application of a vacuum across the walls of the device, thereby forcing cells into the porous structure. Cells further can be incorporated by culturing the device in cell culture medium comprising the cells to be seeded onto the device. In any case, one of ordinary skill can incorporate cells into the device ("seed the device") by any useful method, as are broadly-known in the field of the invention. In one aspect, a compact seeding device is used, essentially as described in Soletti et al. ("A seeding device for tissue engineered tubular structures" *Biomaterials* 27, 2006), which combines synergic action of vacuum, rotation and flow; providing a rapid and uniform seeding of tubular porous structures with no generation of injurious mechanical conditions for cells.

In certain aspects, one or more layers of the device independently comprise a therapeutic agent. For example, at least one therapeutic agent is added to the ECM gel composition, or otherwise included within or at the second, middle layer, and/or is added to or otherwise combined with or included within the first and third layers, e.g. the inner or outer layer of the device. Generally, the therapeutic agents include any substance that can be coated on, embedded into, absorbed into, adsorbed to, or otherwise attached to or incorporated onto or into one or more layers of the multilayer device described herein. Non-limiting examples of such therapeutic agents include antimicrobial agents, anti-inflammatory agents, growth factors, cytokines, antibodies or other binding reagents, cofactors, and steroids. Each therapeutic agent may be used alone or in combination with other therapeutic agents, independently in one or more layers.

In certain non-limiting aspects, the therapeutic agent is a growth factor, such as a neurotrophic or angiogenic factor, which optionally may be prepared using recombinant techniques. Non-limiting examples of growth factors include basic fibroblast growth factor (bFGF), acidic fibroblast growth factor (aFGF), vascular endothelial growth factor (VEGF), hepatocyte growth factor (HGF), insulin-like growth factors 1 and 2 (IGF-1 and IGF-2), platelet derived growth factor (PDGF), stromal derived factor 1 alpha (SDF-1 alpha), nerve growth factor (NGF), ciliary neurotrophic factor (CNTF), neurotrophin-3, neurotrophin-4, neurotrophin-5, pleiotrophin protein (neurite growth-promoting factor 1), midkine protein (neurite growth-promoting factor 2), brain-derived neurotrophic factor (BDNF), tumor angiogenesis factor (TAF), corticotrophin releasing factor (CRF), transforming growth factors $\alpha$ and $\beta$ (TGF-$\alpha$ and TGF-$\beta$), interleukin-8 (IL-8), granulocyte-macrophage colony stimulating factor (GM-CSF), interleukins, and interferons. Commercial preparations of various growth factors, including neurotrophic and angiogenic factors, are available from R & D Systems, Minneapolis, Minnesota; Biovision, Inc, Mountain View, California; ProSpec-Tany TechnoGene Ltd., Rehovot, Israel; and Cell Sciences®, Canton, Massachusetts.

In certain non-limiting aspects, the therapeutic agent is an antimicrobial agent, such as, without limitation, isoniazid, ethambutol, pyrazinamide, streptomycin, clofazimine, rifabutin, fluoroquinolones, ofloxacin, sparfloxacin, rifampin, azithromycin, clarithromycin, dapsone, tetracycline, erythromycin, ciprofloxacin, doxycycline, ampicillin, amphotericin B, ketoconazole, fluconazole, pyrimethamine, sulfadiazine, clindamycin, lincomycin, pentamidine, atovaquone, paromomycin, diclazaril, acyclovir, trifluorouridine, foscarnet, penicillin, gentamicin, ganciclovir, iatroconazole, miconazole, Zn-pyrithione, and silver salts such as chloride, bromide, iodide and periodate.

In certain non-limiting aspects, the therapeutic agent is an anti-inflammatory agent, such as, without limitation, an NSAID, such as salicylic acid, indomethacin, sodium indomethacin trihydrate, salicylamide, naproxen, colchicine, fenoprofen, sulindac, diflunisal, diclofenac, indoprofen, sodium salicylamide; an anti-inflammatory cytokine; an anti-inflammatory protein; a steroidal anti-inflammatory agent; or an anti-clotting agents, such as heparin. Other drugs that may promote wound healing and/or tissue regeneration may also be included.

Any useful cytokine, chemoattractant, drug or cells can be mixed into, mixed with, co-applied or otherwise combined with or incorporated into any device as described herein. For example and without limitation, useful components include growth factors, interferons, interleukins, chemokines, monokines, hormones, angiogenic factors, drugs, and antibiotics.

As used herein, the terms "drug" and "drugs" refer to any compositions having a preventative or therapeutic effect, including and without limitation, antibiotics, peptides, hormones, organic molecules, vitamins, supplements, factors, proteins, and chemoattractants.

In one aspect, a TEVG device is provided having an inner diameter of 2 mm and an outer diameter of 3 mm, a wall thickness of 0.5 mm and an average length of 2 cm. The three graft layers were processed with: 1) electrospinning (ES); 2) thermal induced phase separation (TIPS); 3) molding of decellularized cardiac tissue gel (cECM). Each layer was modeled to duplicate the native tunicae (e.g. intima, media, adventitia) function. Degradable PEUU has been synthesized as previously described in (J. Guan, et al., Synthesis, characterization, and cytocompatibility of elastomeric, biodegradable poly(esterurethane) ureas based on poly(caprolactone) and putrescine, Journal of Biomedical Materials Research 61(3) (2002) 493-503). The electrospinning protocol in (J. T. Krawiec, et al., In vivo functional evaluation of tissue-engineered vascular grafts fabricated using human adipose-derived stem cells from high cardiovascular risk populations, Tissue Engineering Part A 22(9-10) (2016) 765-775) was used to fabricate the first layer (tunica intima). Different layer thickness were produced in order to tune scaffold suture retention properties. The TIPS layer (tunica adventitia) was processed as described in (L. Soletti, et al., A bilayered elastomeric scaffold for tissue engineering of small diameter vascular grafts, Acta Biomaterialia 6(1) (2010) 110-122) with a custom-made mold, made of a stainless steel rod (ID 3.8 mm) covered with poly(tetrafluoroethylene) (PTFE) tubing and concentrically aligned with a tubular glass sheath using two PTFE sealing stoppers. Decellularized ECM solution with concentration of 15 mg/mL was obtained as reported in (A. D'Amore, et al., Bi-layered polyurethane-Extracellular matrix cardiac patch improves ischemic ventricular wall remodeling in a rat model, Biomaterials 107 (2016) 1-14).

According to one aspect of the invention a method of producing, repairing or replacing a tissue in a patient is provided. The method comprises implanting in the patient any aspect of the device as described herein. In one aspect, the device is tubular. In another aspect, the device is anastamosed to a blood vessel of the patient, for example to repair an injured or occluded vessel to treat an ischemic condition in the patient. In one aspect, the device is anastomosed to a coronary artery. In a further aspect, the patient may be is suffering from an ischemic event, such as an embolism, thrombosis, stenosis, or restenosis. In yet another aspect, the ischemic event is a coronary artery disease, such as a myocardial infarction, and the device is anastamosed to a coronary artery. Also provided is a kit comprising the device according to any aspect as described herein. The device is packaged in suitable packaging, such as a foil and/or plastic pouch or container, such as a mylar-containing package, e.g. according to any acceptable and/or appropriate aspect as are broadly-known in the medical device arts for sterile packaging, storing, distributing, and otherwise handling bandages or implants.

Preparation and Testing of a Multi-Layer TEVG

Figure 2:
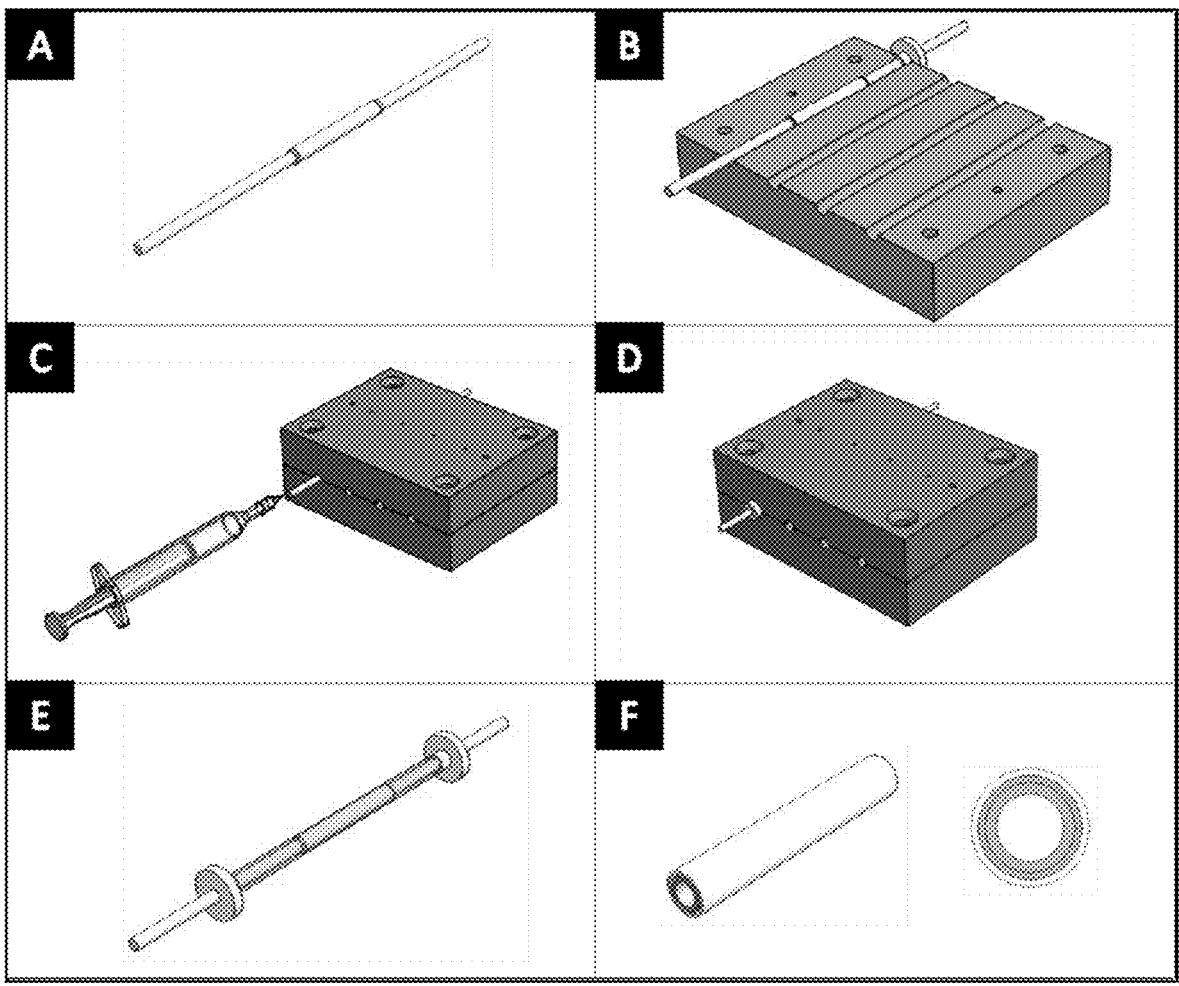
FIG. 2: Schematic of the 3 layer scaffold fabrication process. LAYERS 1-3. A) The electrospun layer is positioned on a steel rod and secured with sutures at the edges. B) The sample is inserted into a custom-made mold and maintained coaxial with the mold cavity. D) ECM gel solution is injected into the mold. D) The mold is closed and rests overnight in an incubator at 37° C. so that the ECM solution can transition to the gel state. E) the second graft layer made of ECM gel is then formed. F) TIPS outer layer is gently slipped on the gel layer so that the three-layered structure is obtained.
Figure 3:
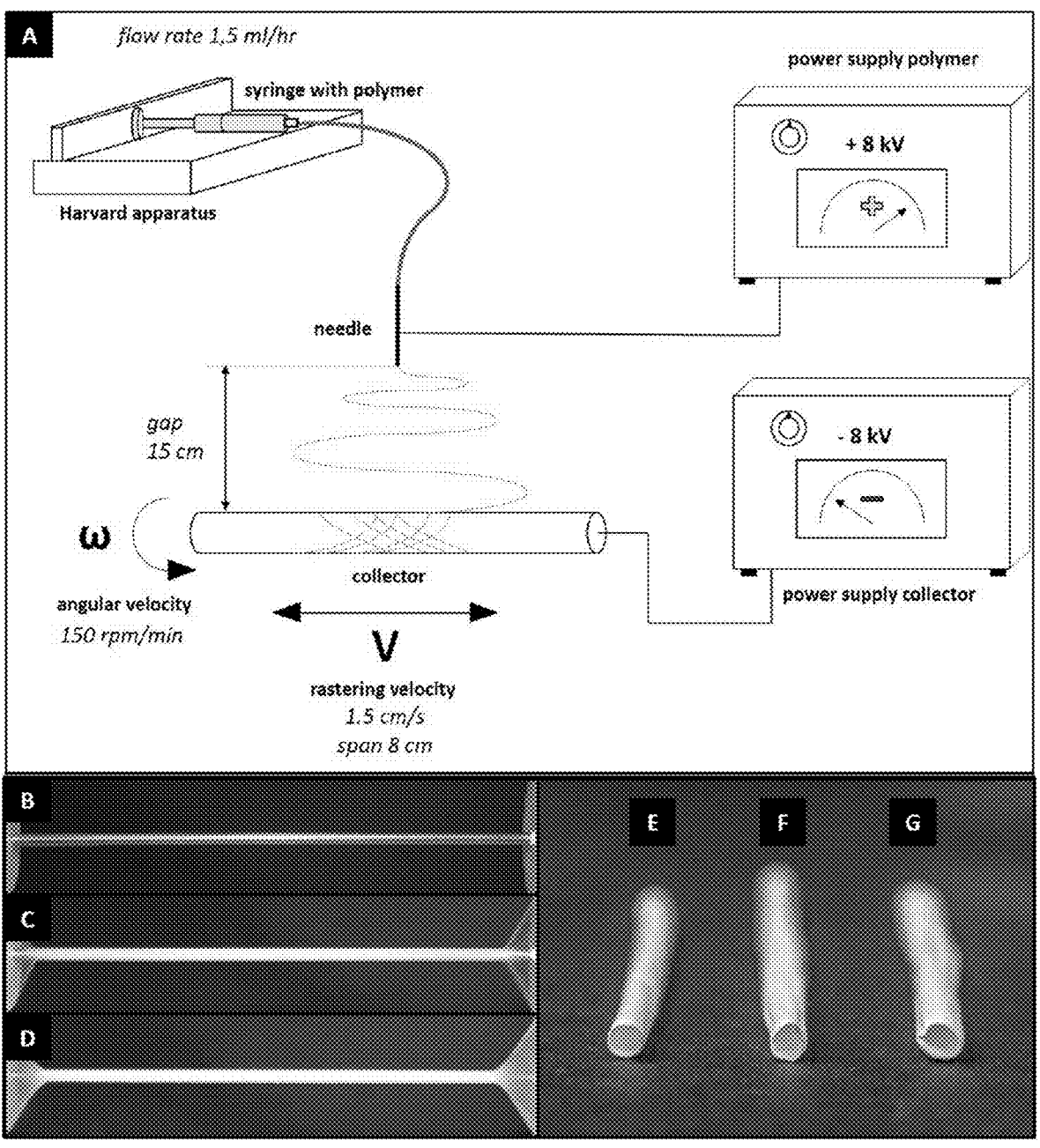
FIG. 3: Schematic of the electrospinning setup. LAYER 1 formation. A) Processing variables utilized for layer one fabrication (Tunica Intima). B) Electrospinning deposition at t=0, C) t=10 min, and D) t=20 min. Electrospun layers with 3 different thicknesses: E) 100 μm, F) 200 μm, and G) 300 μm.
Figure 4:
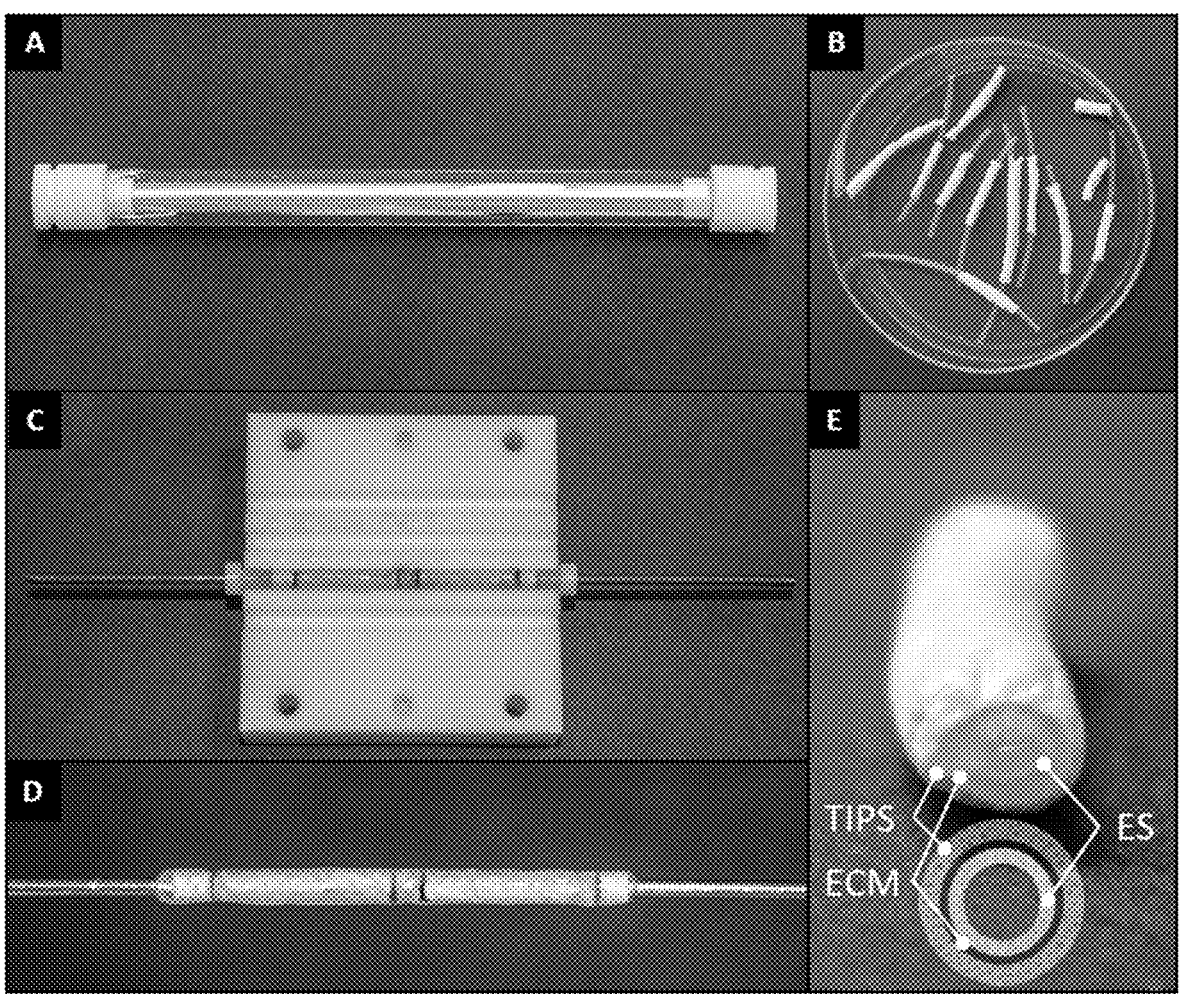
FIG. 4: LAYERS 2-3 formation. A) TIPS mold: metal rod 3.8 mm, thickness PTFE tubing 0.8 mm, glass tube ID 6 mm. B) PEUU TIPS layer for tunica adventitia with ID 3.5 mm. C) gel layer formed around the electrospun layer on the mold. D) Detail of the ECM gel layer. E) Three-layered small-diameter vascular graft (layer 1: electrospun, layer 2 ECM gel, layer 3 TIPS).

The full processing cascade is summarized in FIG. 2. Briefly, the electrospun layer (see FIG. 3 for additional details on electrospinning) is positioned on a steel rod and secured with sutures at the edges (panel A). The sample is then inserted into the custom-made mold and maintained co-axial with the mold cavity (panel B). ECM gel solution is injected into the mold (panel C). The mold is closed and left overnight in an incubator at 37° C. so that the ECM solution can transition to the gel state (panel D). Finally, the sample is removed (panel E) and a TIPS outer layer is gently slipped on the gel layer so that the three-layered structure is obtained (panel F) (see, FIG. 4, panels A-E for photographs of a device as-made).

Figure 5:
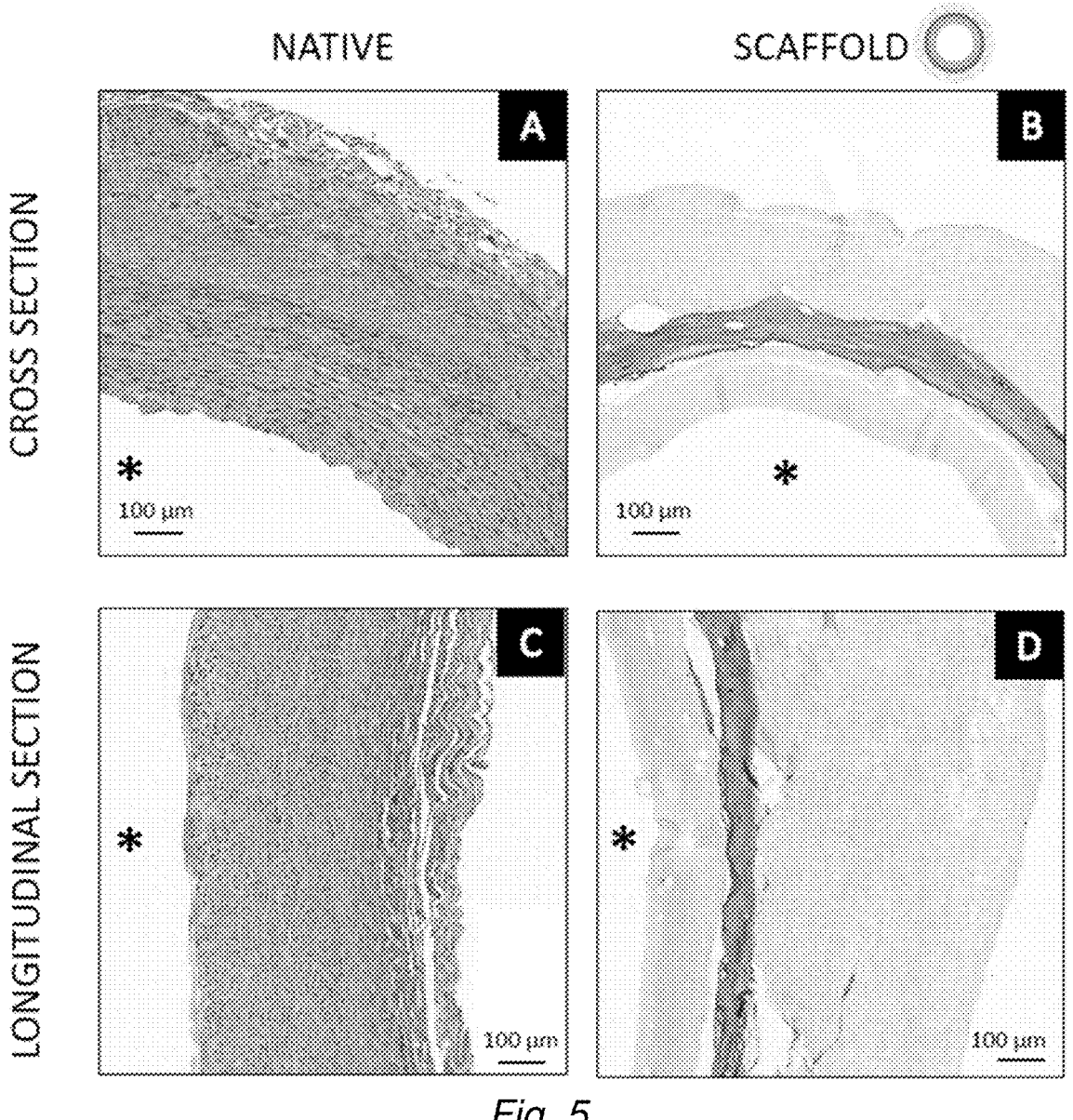
FIG. 5: H&E cross-sections, histological comparison of native vs. engineered graft. A) representative porcine coronary artery cross-section and C) longitudinal section B) engineered graft cross section and D) longitudinal section. Asterisk indicates the lumen side.
Figure 6:
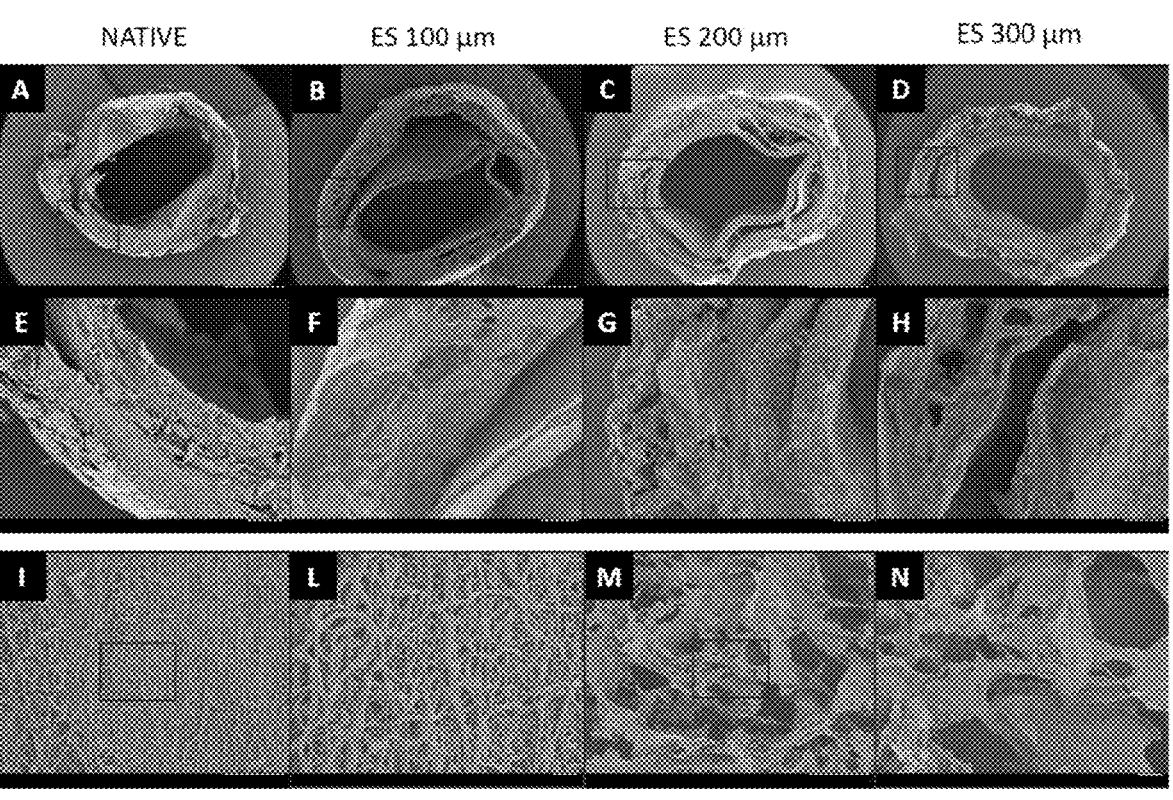
FIG. 6: SEM cross sections native coronary artery vs. engineered graft comparison. A, E) Porcine native vessel with distinct tunica adventitia and tunica media-intima. Capacity to control/modulate vessel global compliance by changing the ES layer: three-layered vascular graft with 3 different ES layer thicknesses including B, F) 100 μm; C, G) 200 μm; D, H) 300 μm. I-L) Detailed view of ES layer morphology and of M-N) TIPS layer morphology.
Figure 7:
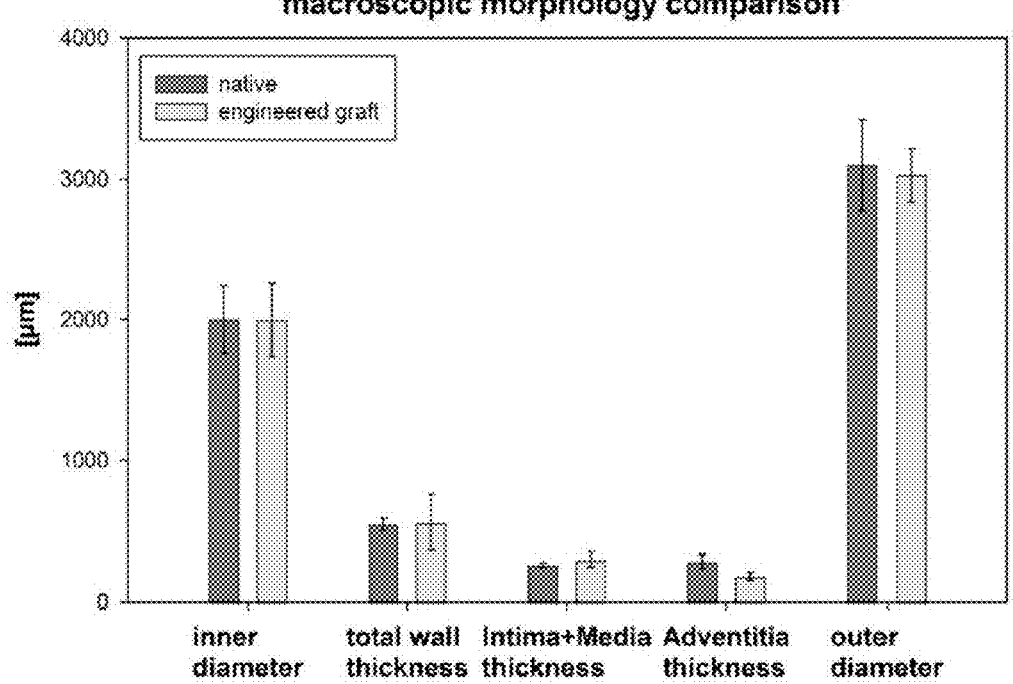
FIG. 7: Macroscopic morphology comparison. Porcine native coronary arteries (n=3) vs. three-layered scaffold (with ES layer measuring 100 μm). Functional heterogeneity has been duplicated in the engineered vascular graft in terms of layers thickness. Results were presented as mean±st. deviation.
Figure 8A:
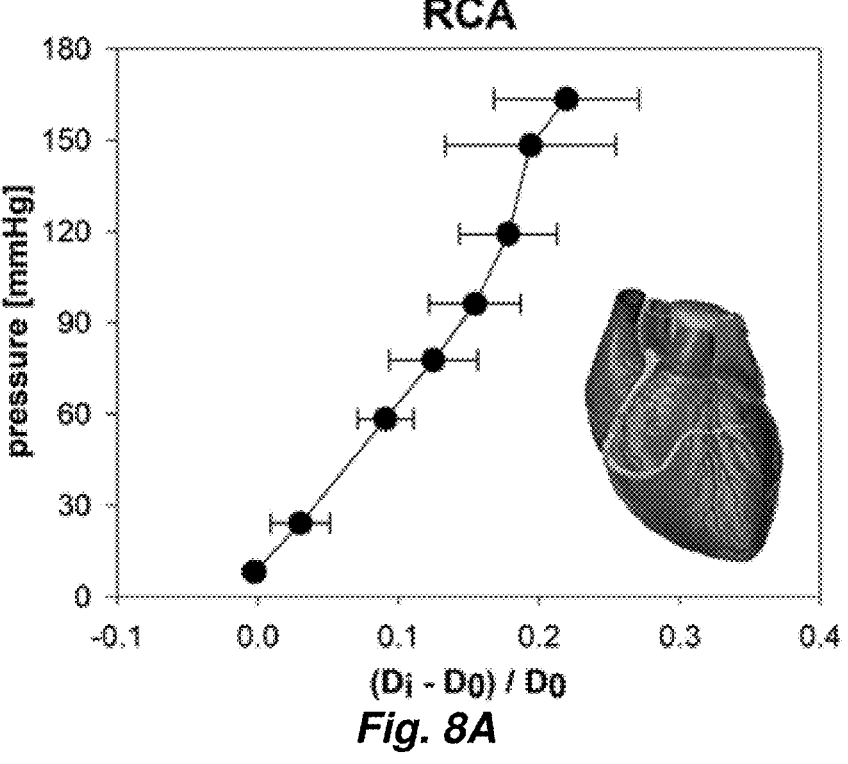
FIGS. 8A-8D: Global mechanical compliance. Pressure-volume test results for porcine coronary arteries.
Figure 8B:
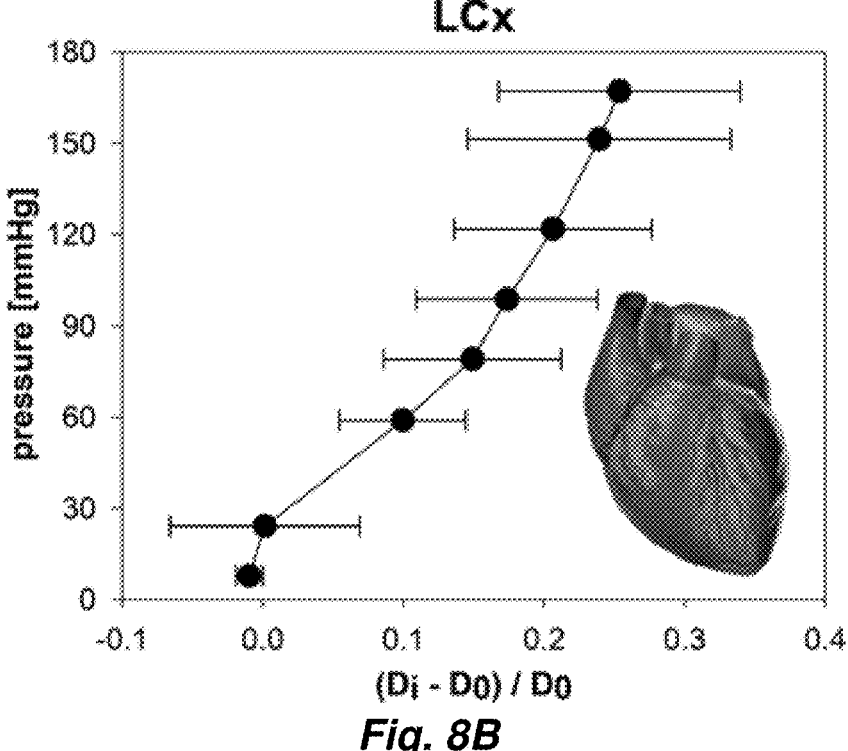
Figure 8C:
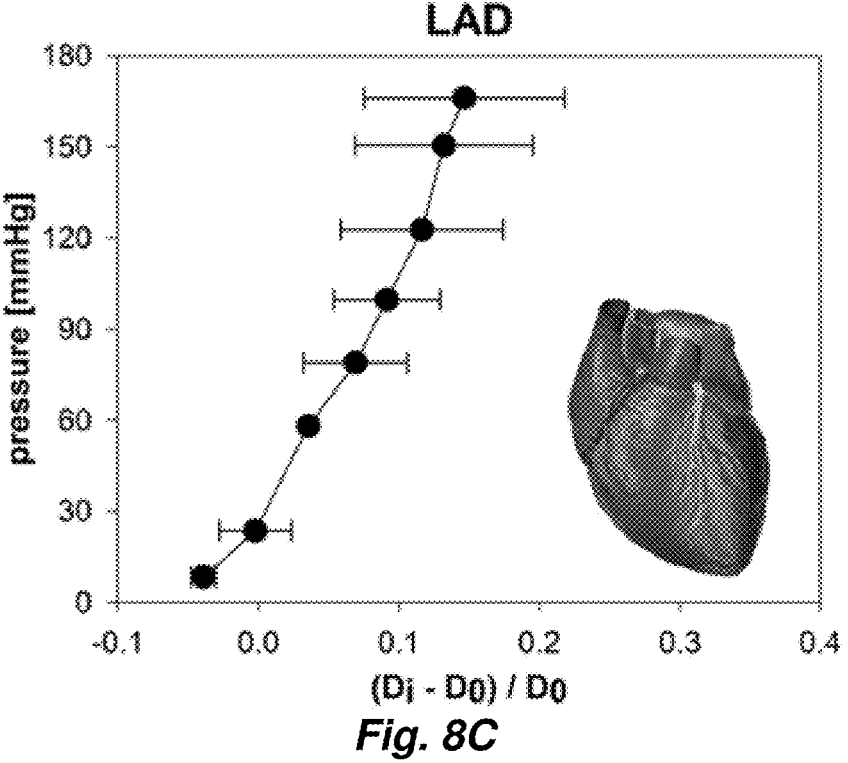
Figure 8D:
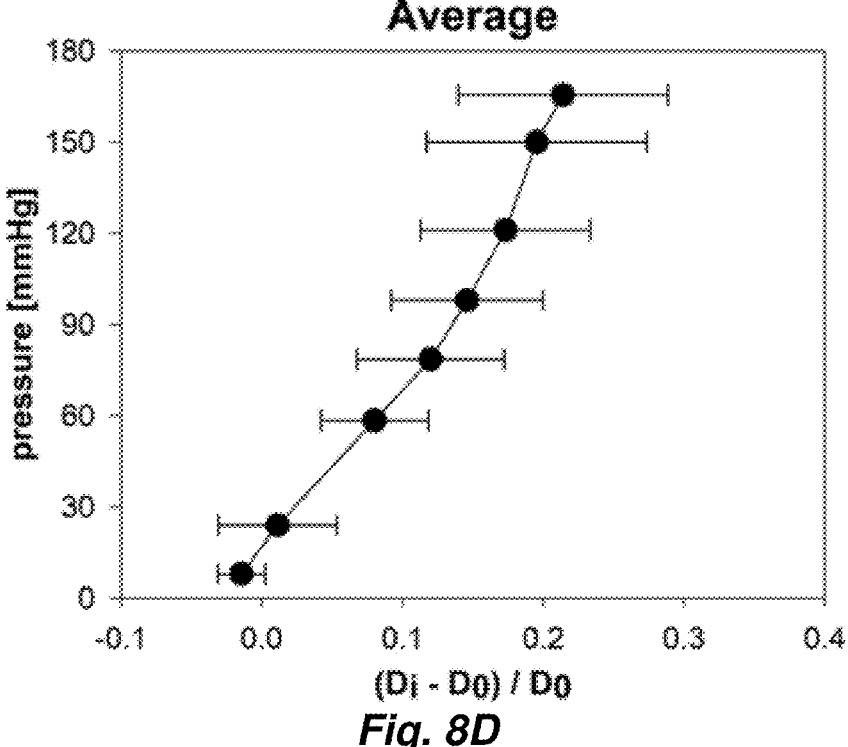
Figure 9A:
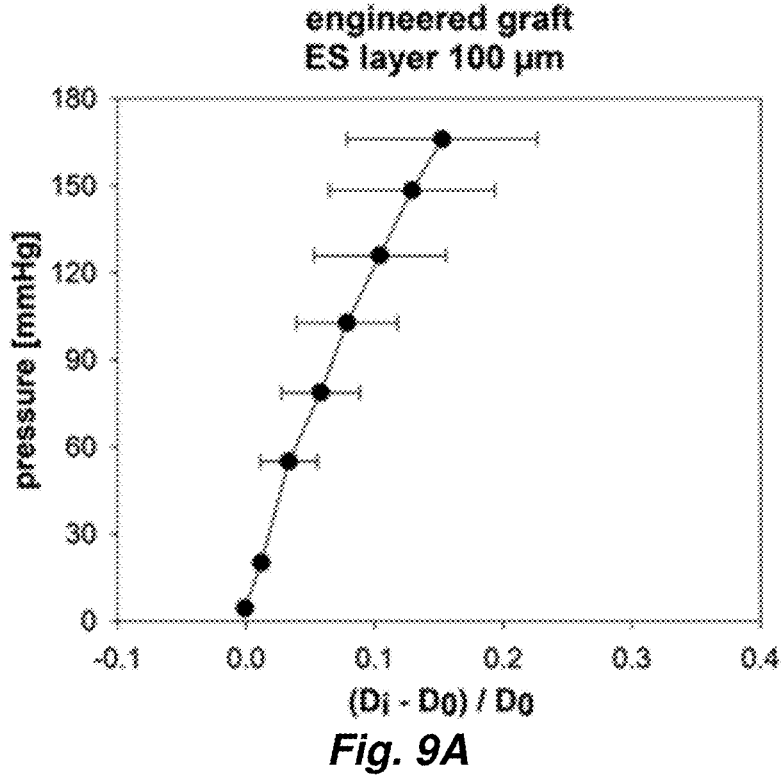
Figure 9B:
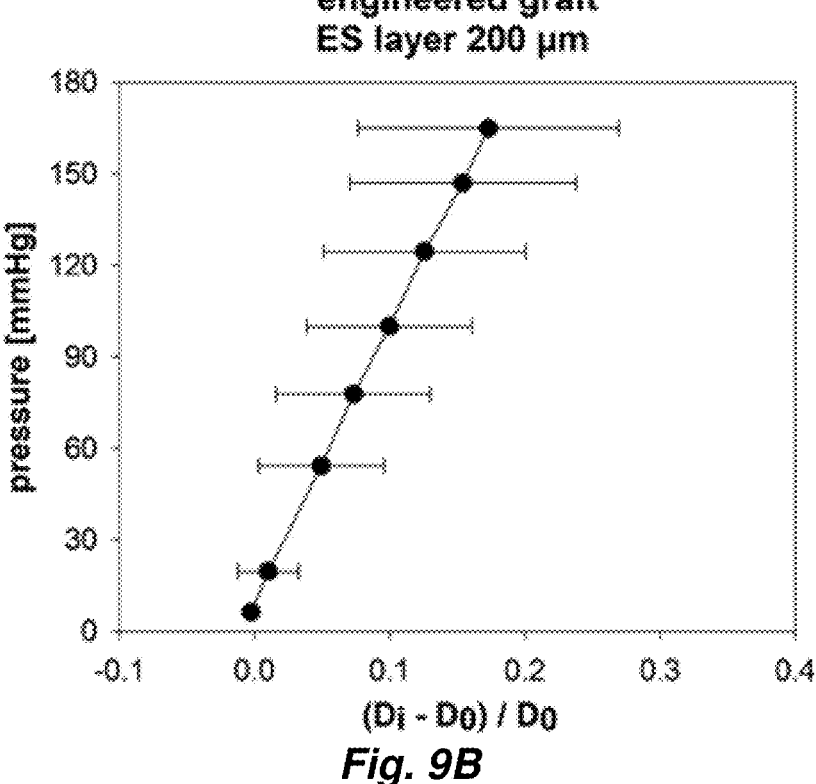
Figure 9C:
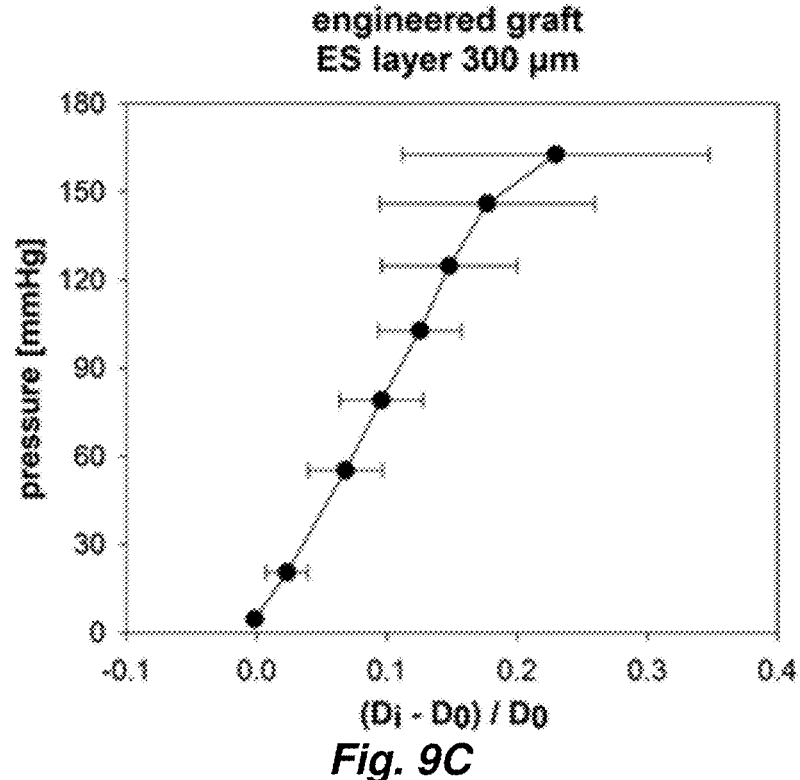
Figure 9D:
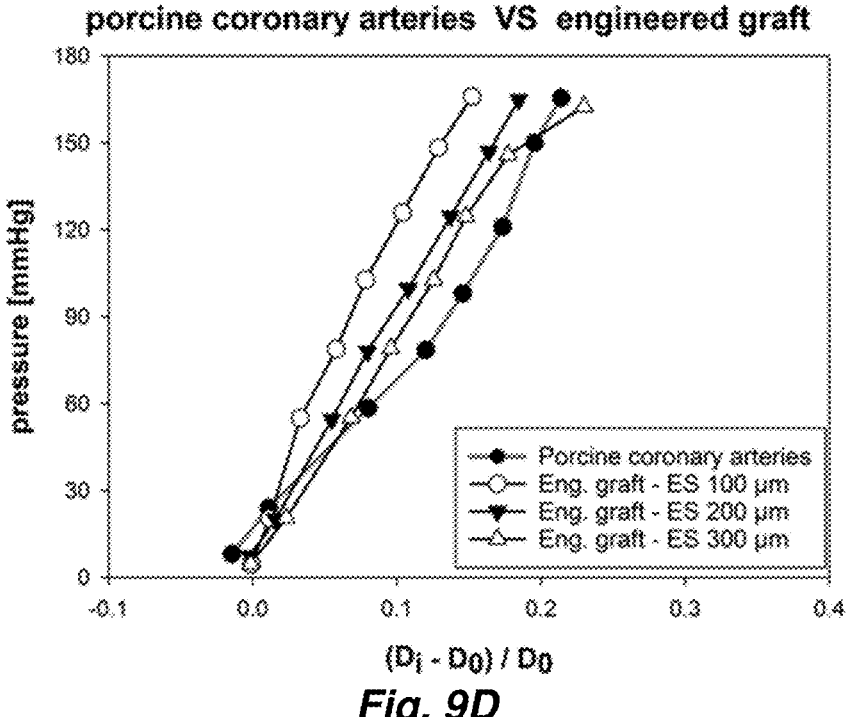
Figure 9E:
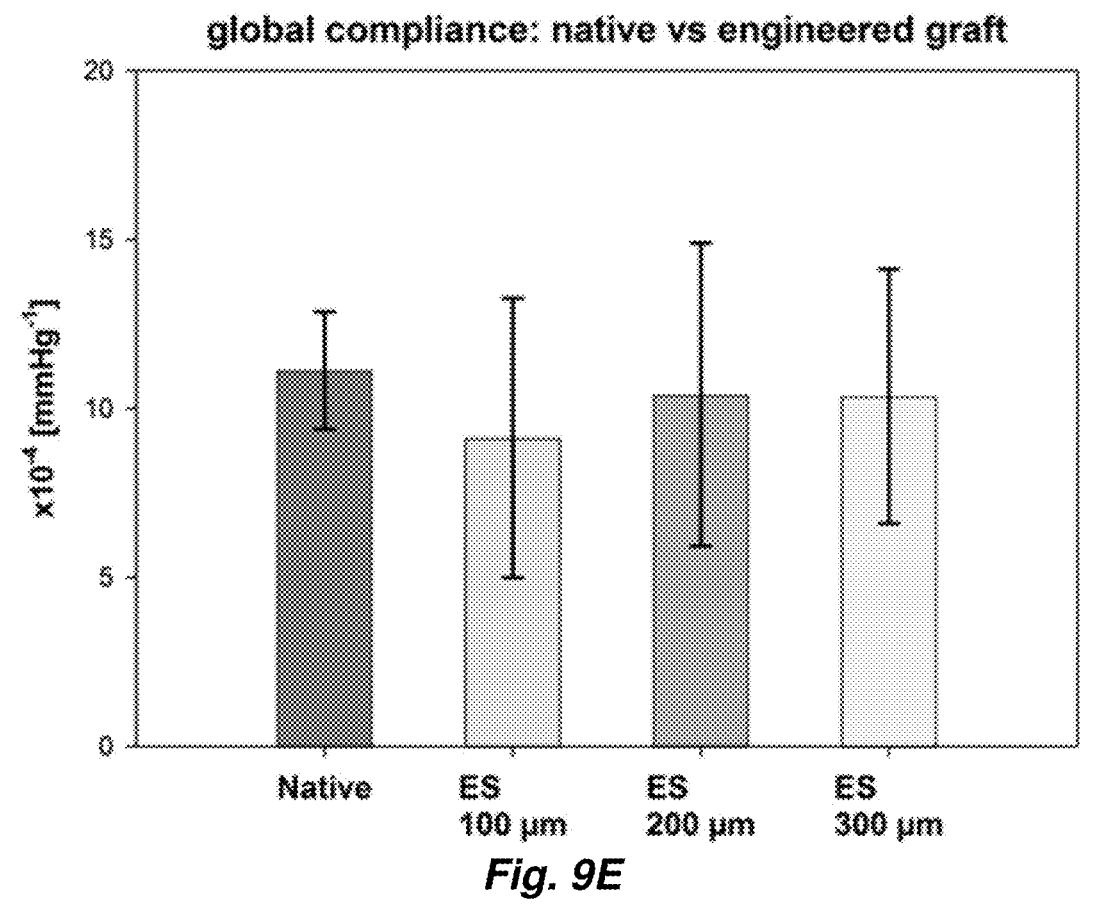
Figure 10A:
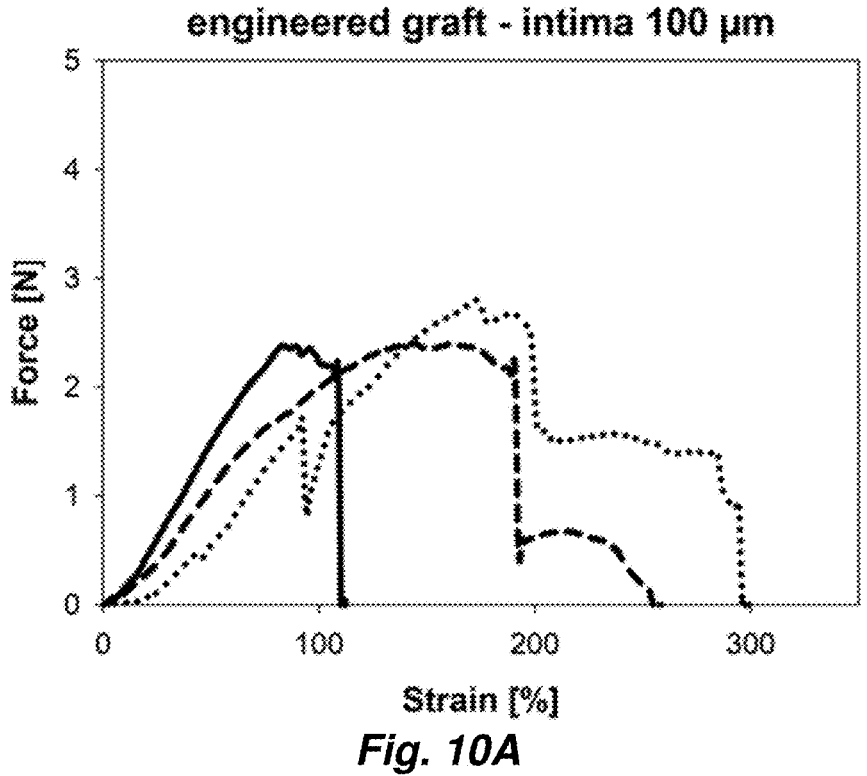
FIGS. 10A-10D: Suture retention test. Impact of ES layer thickness, suture retention characteristics for grafts fabricated with increasing ES thickness including.
Figure 10B:
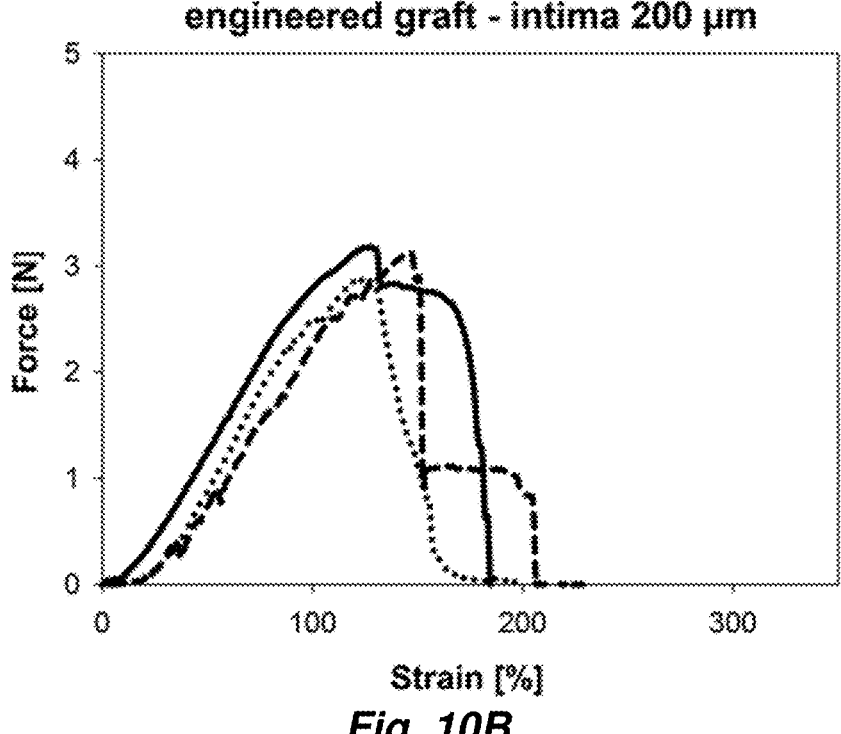
Figure 10C:
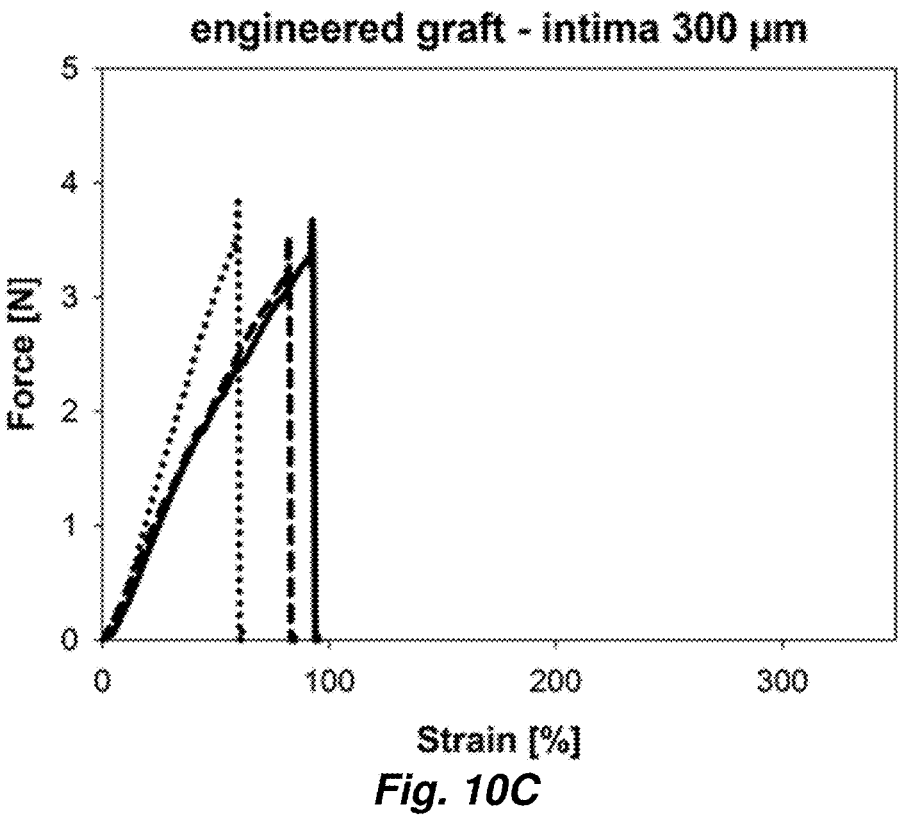
Figure 10D:
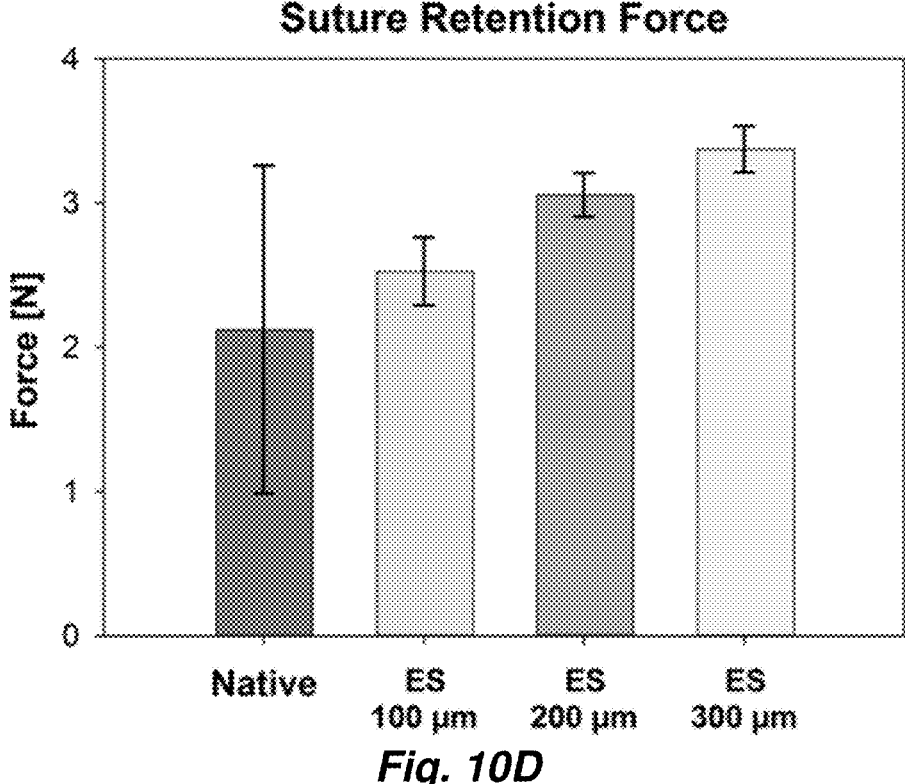

A prototype was fabricated, and evaluation of the native and synthetic vessel were performed. (FIGS. 2-10D) Morphological properties were evaluated with images from histological staining and Scanning Electron Microscopy. Compliance was tested on intact samples approximately 20 mm long with a custom-made pressure-volume test device in the range 80-120 mmHg, as in Ye, S. et al. (Nonthrombogenic, Biodegradable Elastomeric Polyurethanes with Variable Sulfobetaine Content. *ACS Appl. Mater. Interfaces,* 2014, 6 (24), pp 22796-22806). Suture retention force was tested on rectangular specimens (10 mm length, 4 mm width). The short edge of each specimen was originally oriented circumferentially on the tubular scaffold. A single loop of 7-0 poly(propylene) suture was created at approximately 2 mm from the short edge of each sample and secured to a custom-made clamp provided with a hook connected to the clamp of the testing device. A normal clamp was used to fix the other end of the sample to the bottom of the device. An extension rate of 1 mm/s was used to pull the suture. Suture retention strength was taken as the maximum force recorded prior to pull-out of the suture. The results obtained from this characterization and can be summarized as follows:

A. capacity to assess mechanism for in situ tissue regeneration: blood derived host cell recruitment vs. anastomosis derived recruitment. The dry electrospun layer, generally a network with reduced pore size, functions as barrier to cell infiltration. This layer can be positioned as layer proximal or distal to the lumen (intima/adventitia position);

B. capacity to combine synthetic polymeric layers with ECM layer/bioactive component layer to promote tissue formation and mitigate intima hyperplasia;

C. capacity to duplicated functional heterogeneity (e.g., three layer structure including tunica intima, media and adventitia) of native blood vessels at macroscopic-organ level (See, FIG. 7);

D. capacity to duplicate functional heterogeneity (e.g., three layer structure including tunica intima, media and adventitia) of native blood vessels at mesoscopic-tissue level (See, FIG. 5);

E. capacity to duplicated functional heterogeneity (e.g., three layer structure including tunica intima, media and adventitia) of native blood vessels at microscopic-cell level (See, FIG. 6);

F. capacity to modulate/tune global compliance mimicking native tissue mechanical response (See, FIGS. 8 and 9A-9D);

G. capacity to modulate/tune scaffold suture retention mimicking native tissue mechanical properties (See, FIGS. 10A-10D).

The following clauses illustrate various aspects of the invention:

Clause 1. A method of making a synthetic tubular graft device, comprising:

depositing an ECM gel layer over a first tubular, porous, biodegradable polymer matrix; and depositing a second tubular, porous, biodegradable polymer matrix over the ECM gel to produce a tubular structure.

Clause 2. The method of clause 1, wherein the first tubular, porous, biodegradable polymer matrix is a dry-electrospun matrix.

Clause 3. The method of clause 1 or 2, wherein the ECM gel is prepared from vascular tissue.

Clause 4. The method of any of clauses 1-3, wherein the second tubular, porous, biodegradable polymer matrix is prepared by phase separation.

Clause 5. The method of clause 4, wherein the phase separation is thermal-induced phase separation.

Clause 6. The method of any one of clauses 1-5, wherein the first tubular, porous, biodegradable polymer matrix comprises one or more of: poly(lactic acid) (PLA); poly(trimethylene carbonate) (PTMC); poly(caprolactone) (PCL); poly(glycolic acid) (PGA); poly(glycolide-co-trimethylenecarbonate) (PGTMC); poly(L-lactide-co-glycolide) (PLGA); polyethylene-glycol (PEG-) containing block copolymers; polyphosphazene; poly(ester urethane) urea (PEUU); poly(ether ester urethane)urea (PEEUU); poly(ester carbonate)urethane urea (PECUU); poly(carbonate)urethane urea (PCUU); a polyurethane; a polyester; a polymer comprising monomers derived from alpha-hydroxy acids such as: polylactide, poly(lactide-co-glycolide), poly(L-lactide-co-caprolactone), polyglycolic acid, poly(dl-lactide-co-glycolide), and/or poly(l-lactide-co-dl-lactide); a polymer comprising monomers derived from esters including polyhydroxybutyrate, polyhydroxyvalerate, polydioxanone, and/or polyglactin; a polymer comprising monomers derived from lactones; or a polymer comprising monomers derived from carbonates including polycarbonate, polyglyconate, poly(glycolide-co-trimethylene carbonate), or poly(glycolide-co-trimethylene carbonate-co-dioxanone).

Clause 7. The method of any one of clauses 1-6, wherein the second tubular, porous, biodegradable polymer matrix comprises one or more of: poly(lactic acid) (PLA); poly(trimethylene carbonate) (PTMC); poly(caprolactone) (PCL); poly(glycolic acid) (PGA); poly(glycolide-co-trimethylenecarbonate) (PGTMC); poly(L-lactide-co-glycolide) (PLGA); polyethylene-glycol (PEG-) containing block copolymers; polyphosphazene; poly(ester urethane) urea (PEUU); poly(ether ester urethane)urea (PEEUU); poly(ester carbonate)urethane urea (PECUU); poly(carbonate)urethane urea (PCUU); a polyurethane; a polyester; a polymer comprising monomers derived from alpha-hydroxy acids such as: polylactide, poly(lactide-co-glycolide), poly(L-lactide-co-caprolactone), polyglycolic acid, poly(dl-lactide-co-glycolide), and/or poly(l-lactide-co-dl-lactide); a polymer comprising monomers derived from esters including polyhydroxybutyrate, polyhydroxyvalerate, polydioxanone, and/or polyglactin; a polymer comprising monomers derived from lactones; or a polymer comprising monomers derived from carbonates including polycarbonate, polyglyconate, poly(glycolide-co-trimethylene carbonate), or poly(glycolide-co-trimethylene carbonate-co-dioxanone).

Clause 8. The method of clause 1, comprising:

dry electrospinning a poly(ester urethane) urea onto a mandrel to form the first tubular, porous, biodegradable polymer matrix;

placing the mandrel comprising the first tubular, porous, biodegradable polymer matrix within a cylindrical mold having an inside diameter greater than an outside diameter of the first tubular, porous, biodegradable polymer matrix;

depositing an ECM pre-gel about the first tubular, porous, biodegradable polymer matrix;

gelling the ECM pre-gel about the first tubular, porous, biodegradable polymer matrix; and inserting the ECM gel-coated first tubular, porous, biodegradable polymer matrix into a tube of a porous poly(ester urethane) urea matrix.

Clause 9. The method of any one of clauses 1-8, wherein the polymer of one or both of the first tubular, porous, biodegradable polymer matrix and the second tubular, porous, biodegradable polymer matrix comprises one or more of a PEUU, a PEEUU, a PECUU, and a PCUU.

Clause 10. The method of any one of clauses 1-8, wherein the polymer of one or both of the first tubular, porous, biodegradable polymer matrix and the second tubular, porous, biodegradable polymer matrix comprises a PEUU.

Clause 11. The method of any one of clauses 1-10, wherein the first tubular, porous, biodegradable polymer matrix has an inner diameter of from 1 mm to 2 mm, from 1.5 mm to 3.5 mm, or 2 mm.

Clause 12. The method of any one of clauses 1-11, wherein the device has a wall thickness of from 200 μm to 1 mm, from 250 μm to 750 μm, for example 500 μm.

Clause 13. The method of any one of clauses 1-12, wherein the thickness of the combined layers of the first tubular, porous, biodegradable polymer matrix plus the ECM gel ranges from 100 μm to 500 μm, from 150 μm to 350 μm, or from 175 μm to 250 μm.

Clause 14. The method of any one of clauses 1-13, wherein the thickness of the second tubular, porous, biodegradable polymer matrix plus the ECM gel ranges from 50 μm to 250 μm, from 75 μm to 125 μm, for example 100 μm.

Clause 15. The method of any one of clauses 1-14, wherein either or both of the first tubular, porous, biodegradable polymer matrix and the second tubular, porous, biodegradable polymer matrix comprises an anti-thrombogenic polymer composition.

Clause 16. The method of clause 15, wherein the anti-thrombogenic polymer composition comprises a zwitterionic moiety that is optionally pendant from the polymer backbone, wherein the polymer composition optionally is a polyanhydride, a polyester, a polyurethane, PCUU, PECUU, PEUU, PEEUU, or a polyacrylate modified with a zwitterion moiety.

Clause 17. The method of clause 16, wherein the zwitterionic moiety is a sulfobetaine or and phosphorylcholine moiety.

Clause 18. A multi-layer synthetic graft device comprising:

a first porous, biodegradable polymer matrix;

an ECM gel layer over the first porous, biodegradable polymer matrix; and a second porous, biodegradable polymer matrix over the ECM gel.

Clause 19. A multi-layer synthetic graft device comprising:

a first tubular, porous, biodegradable polymer matrix;

an ECM gel layer disposed circumferentially about the first tubular, porous, biodegradable polymer matrix; and a second tubular, porous, biodegradable polymer matrix disposed circumferentially about the ECM gel.

Clause 20. The device of clause 18 or 19, wherein the first tubular, porous, biodegradable polymer matrix is a dry-electrospun matrix.

Clause 21. The device of any one of clauses 18-20, wherein the ECM gel is prepared from vascular tissue.

Clause 22. The device of any one of clauses 18-21, wherein the second tubular, porous, biodegradable polymer matrix is prepared by thermally induced phase separation.

Clause 23. The device of clause 22, wherein the phase separation is thermal-induced phase separation.

Clause 24. The device of any one of clauses 18-23, wherein the first tubular, porous, biodegradable polymer matrix comprises one or more of: poly(lactic acid) (PLA); poly(trimethylene carbonate) (PTMC); poly(caprolactone) (PCL); poly(glycolic acid) (PGA); poly(glycolide-co-trimethylenecarbonate) (PGTMC); poly(L-lactide-co-glycolide) (PLGA); polyethylene-glycol (PEG-) containing block copolymers; polyphosphazene; poly(ester urethane) urea (PEUU); poly(ether ester urethane)urea (PEEUU); poly(ester carbonate)urethane urea (PECUU); poly(carbonate)urethane urea (PCUU); a polyurethane; a polyester; a polymer comprising monomers derived from alpha-hydroxy acids such as: polylactide, poly(lactide-co-glycolide), poly(L-lactide-co-caprolactone), polyglycolic acid, poly(dl-lactide-co-glycolide), and/or poly(I-lactide-co-dl-lactide); a polymer comprising monomers derived from esters including polyhydroxybutyrate, polyhydroxyvalerate, polydioxanone, and/or polyglactin; a polymer comprising monomers derived from lactones; or a polymer comprising monomers derived from carbonates including polycarbonate, polyglyconate, poly(glycolide-co-trimethylene carbonate), or poly(glycolide-co-trimethylene carbonate-co-dioxanone).

Clause 25. The device of any one of clauses 18-24, wherein the second tubular, porous, biodegradable polymer matrix comprises one or more of: poly(lactic acid) (PLA); poly(trimethylene carbonate) (PTMC); poly(caprolactone) (PCL); poly(glycolic acid) (PGA); poly(glycolide-co-trimethylenecarbonate) (PGTMC); poly(L-lactide-co-glycolide) (PLGA); polyethylene-glycol (PEG-) containing block copolymers; polyphosphazene; poly(ester urethane) urea (PEUU); poly(ether ester urethane)urea (PEEUU); poly(ester carbonate)urethane urea (PECUU); poly(carbonate)urethane urea (PCUU); a polyurethane; a polyester; a polymer comprising monomers derived from alpha-hydroxy acids such as: polylactide, poly(lactide-co-glycolide), poly(L-lactide-co-caprolactone), polyglycolic acid, poly(dl-lactide-co-glycolide), and/or poly(I-lactide-co-dl-lactide); a polymer comprising monomers derived from esters including polyhydroxybutyrate, polyhydroxyvalerate, polydioxanone, and/or polyglactin; a polymer comprising monomers derived from lactones; or a polymer comprising monomers derived from carbonates including polycarbonate, polyglyconate, poly(glycolide-co-trimethylene carbonate), or poly(glycolide-co-trimethylene carbonate-co-dioxanone).

Clause 26. The device of any one of clauses 18-25, wherein the polymer of one or both of the first tubular, porous, biodegradable polymer matrix and the second tubular, porous, biodegradable polymer matrix comprises one or more of a PEUU, a PEEUU, a PECUU, and a PCUU.

Clause 27. The device of any one of clauses 18-25, wherein the polymer of one or both of the first tubular, porous, biodegradable polymer matrix and the second tubular, porous, biodegradable polymer matrix comprises a PEUU.

Clause 28. The device of any one of clauses 18-27, wherein the first tubular, porous, biodegradable polymer matrix has an inner diameter ranging from 1 mm to 2 mm, from 1.5 mm to 3.5 mm, or 2 mm.

Clause 29. The device of any one of clauses 18-28, wherein the device has a wall thickness of from 200 μm to 1 mm, from 250 μm to 750 μm, for example 500 μm.

Clause 30. The device of any one of clauses 18-29, wherein the thickness of the combined layers of the first tubular, porous, biodegradable polymer matrix plus the ECM gel ranges from 100 μm to 500 μm, from 150 μm to 350 μm, or from 175 μm to 250 μm.

Clause 31. The device of any one of clauses 18-30, wherein the thickness of the second tubular, porous, biodegradable polymer matrix plus the ECM gel ranges from 50 μm to 250 μm, from 75 μm to 125 μm, for example 100 μm.

Clause 32. The device of any one of clauses 18-31, wherein either or both of the first tubular, porous, biodegradable polymer matrix and the second tubular, porous, biodegradable polymer matrix comprises an anti-thrombogenic polymer composition.

Clause 33. The device of clause 32, wherein the anti-thrombogenic polymer composition comprises a zwitterionic moiety that is optionally pendant from the polymer backbone, wherein the polymer composition optionally is a polyanhydride, a polyester, a polyurethane, PCUU, PECUU, PEUU, PEEUU, or a polyacrylate modified with a zwitterion moiety.

Clause 34. The device of clause 33, wherein the zwitterionic moiety is a sulfobetaine or and phosphorylcholine moiety.

Clause 35. A method of producing, repairing or replacing a tissue in a patient, comprising implanting in the patient the device of any one of clauses 18-34 in the patient.

Clause 36. The method of clause 35, wherein the device is tubular.

Clause 37. The method of clause 35 or 36, wherein the device is anastamosed to a blood vessel of the patient.

Clause 38. The method of any one of clauses 35-37, wherein the device is anastomosed to a coronary artery.

Clause 39. The method of any one of clauses 35-38, wherein the patient is suffering from an ischemic event, such as an embolism, thrombosis, stenosis, or restenosis.

Clause 40. The method of clause 39, wherein the ischemic event is a coronary artery disease, such as a myocardial infarction, and the device is anastamosed to a coronary artery.

Clause 41. A kit comprising the device according to any one of clauses 18-34 in suitable packaging, such as a foil and/or plastic pouch or container, such as a Mylar package.

While the present invention is described with reference to several distinct embodiments, those skilled in the art may make modifications and alterations without departing from the scope and spirit. Accordingly, the above detailed description is intended to be illustrative rather than restrictive.

We claim:

1. A multi-layer synthetic graft device comprising:

a first tubular, porous, biodegradable polymer matrix, the first tubular, porous, biodegradable polymer matrix formed by electrospinning and configured to prevent cellular migration therethrough;

an ECM gel layer disposed circumferentially about the first porous, biodegradable polymer matrix; and a second tubular, porous, biodegradable polymer matrix disposed circumferentially about the ECM gel, the second tubular, porous, biodegradable polymer matrix formed by thermally induced phase separation and configured to permit cellular migration therethrough.

2. The device of claim 1, wherein a thickness of the first tubular, porous, biodegradable polymer matrix is at least 100 μm.

3. The device of claim 2, wherein a suture retention force of the device is more than 2N.

4. The device of claim 1, wherein the ECM gel is prepared from vascular tissue.

5. The device of claim 1, wherein the first tubular, porous, biodegradable polymer matrix, and/or the second tubular, porous, biodegradable polymer matrix comprises one or more of: poly(lactic acid) (PLA); poly(trimethylene carbonate) (PTMC); poly(caprolactone) (PCL); poly(glycolic acid) (PGA); poly(glycolide-co-trimethylenecarbonate) (PGTMC); poly(L-lactide-co-glycolide) (PLGA); polyethylene-glycol (PEG-) containing block copolymers; polyphosphazene; poly(ester urethane) urea (PEUU); poly(ether ester urethane) urea (PEEUU); poly(ester carbonate) urethane urea (PECUU); poly(carbonate) urethane urea (PCUU); a polyurethane; a polyester; a polymer comprising monomers derived from alpha-hydroxy acids such as: polylactide, poly(lactide-co-glycolide), poly(L-lactide-co-caprolactone), polyglycolic acid, poly(dl-lactide-co-glycolide), and/or poly(l-lactide-co-dl-lactide); a polymer comprising monomers derived from esters including polyhydroxybutyrate, polyhydroxyvalerate, polydioxanone, and/or polyglactin; a polymer comprising monomers derived from lactones; or a polymer comprising monomers derived from carbonates including polycarbonate, polyglyconate, poly (glycolide-co-trimethylene carbonate), or poly(glycolide-co-trimethylene carbonate-co-dioxanone).

6. The device of claim 1, wherein the first tubular, porous, biodegradable polymer matrix and the second tubular, porous, biodegradable polymer matrix comprise PCUU.

7. The device of claim 1, wherein:

the first tubular, porous, biodegradable polymer matrix has an inner diameter ranging from 1 mm to 2 mm;

the device has a total thickness of from 200 μm to 1 mm;

a thickness of the combined layers of the first tubular, porous, biodegradable polymer matrix plus the ECM gel ranges from 100 μm to 500 μm; or a thickness of the second tubular, porous, biodegradable polymer matrix plus the ECM gel ranges from 50 μm to 250 μm.

8. The device of claim 1, wherein one or both of the first tubular, porous, biodegradable polymer matrix and the second tubular, porous, biodegradable polymer matrix comprises an anti-thrombogenic polymer composition.

9. The device of claim 1, comprising:

a first tubular layer of a porous, biodegradable polymer matrix formed by electrospinning and configured to prevent cellular migration therethrough;

a layer of vascular ECM gel disposed circumferentially about the first tubular layer; and a second tubular layer of a porous, biodegradable polymer matrix disposed circumferentially about the ECM gel, the second tubular layer formed from PEUU by thermally-induced phase separation, the second tubular layer configured to permit cellular migration therethrough, wherein a thickness of the first layer and the layer of vascular ECM gel ranges from 150 μm to 350 μm.

10. A method of making a synthetic tubular graft device, comprising:

forming a first tubular, porous, biodegradable polymer matrix by electrospinning;

depositing an ECM gel layer over the first tubular, porous, biodegradable polymer matrix to produce a tubular, multi-layer structure; and inserting the tubular, multi-layer structure into a second, tubular, porous, biodegradable polymer matrix formed by thermal induced phase separation, thereby producing a tubular graft device.

11. The method of claim 10, wherein the first tubular, porous, biodegradable polymer matrix is a dry-electrospun matrix.

12. The method of claim 10, wherein the ECM gel is prepared from vascular tissue.

13. The method of claim 10, wherein the first tubular, porous, biodegradable polymer matrix and/or the second tubular, porous, biodegradable polymer matrix comprises one or more of: poly(lactic acid) (PLA); poly(trimethylene carbonate) (PTMC); poly(caprolactone) (PCL); poly(glycolic acid) (PGA); poly(glycolide-co-trimethylenecarbonate) (PGTMC); poly(L-lactide-co-glycolide) (PLGA); polyethylene-glycol (PEG-) containing block copolymers; polyphosphazene; poly(ester urethane) urea (PEUU); poly (ether ester urethane) urea (PEEUU); poly(ester carbonate) urethane urea (PECUU); poly(carbonate) urethane urea (PCUU); a polyurethane; a polyester; a polymer comprising monomers derived from alpha-hydroxy acids such as: polylactide, poly(lactide-co-glycolide), poly(L-lactide-co-caprolactone), polyglycolic acid, poly(dl-lactide-co-glycolide), and/or poly(l-lactide-co-dl-lactide); a polymer comprising monomers derived from esters including polyhydroxybutyrate, polyhydroxyvalerate, polydioxanone, and/or polyglactin; a polymer comprising monomers derived from lactones; or a polymer comprising monomers derived from carbonates including polycarbonate, polyglyconate, poly (glycolide-co-trimethylene carbonate), or poly(glycolide-co-trimethylene carbonate-co-dioxanone).

14. The method of claim 10, wherein the first tubular, porous, biodegradable polymer matrix and the second tubular, porous, biodegradable polymer matrix comprise PCUU.

15. The method of claim 10, comprising:

dry electrospinning a PCUU onto a mandrel to form the first tubular, porous, biodegradable polymer matrix;

placing the mandrel comprising the first tubular, porous, biodegradable polymer matrix within a cylindrical mold having an inside diameter greater than an outside diameter of the first tubular, porous, biodegradable polymer matrix;

depositing an ECM pre-gel about the first tubular, porous, biodegradable polymer matrix;

gelling the ECM pre-gel about the first tubular, porous, biodegradable polymer matrix; and inserting the ECM gel-coated first tubular, porous, biodegradable polymer matrix into the second tubular, porous, biodegradable polymer matrix, wherein the second tubular, porous, biodegradable polymer matrix comprises a PCUU matrix.

16. The method of claim 10, wherein:

the first tubular, porous, biodegradable polymer matrix has an inner diameter of from 1 mm to 2 mm;

the device has a wall thickness of from 200 μm to 1 mm;

a thickness of the combined layers of the first tubular, porous, biodegradable polymer matrix plus the ECM gel ranges from 100 μm to 500 μm; or a thickness of the second tubular, porous, biodegradable polymer matrix plus the ECM gel ranges from 50 μm to 250 μm.

17. The method of claim 10, wherein one or both of the first tubular, porous, biodegradable polymer matrix and the second tubular, porous, biodegradable polymer matrix comprises an anti-thrombogenic polymer composition.

18. The method of claim 10, wherein a thickness of the first tubular, porous, biodegradable polymer matrix is at least 100 μm.

19. The method of claim 18, wherein a suture retention force of the device is more than 2N.

* * * * *